(12) United States Patent
Luo et al.

(10) Patent No.: US 10,030,083 B2
(45) Date of Patent: Jul. 24, 2018

(54) POLYMERS FUNCTIONALIZED WITH PROTECTED OXIME COMPOUNDS CONTAINING A CYANO GROUP

(71) Applicant: BRIDGESTONE CORPORATION, Chuo-Ku (JP)

(72) Inventors: Steven Luo, Copley, OH (US); Joshua S. Dickstein, Copley, OH (US)

(73) Assignee: Bridgestone Corporation, Chuo-ku (JP)

(*) Notice: Subject to any disclaimer, the term of this patent is extended or adjusted under 35 U.S.C. 154(b) by 460 days.

(21) Appl. No.: 14/704,318

(22) Filed: May 5, 2015

(65) Prior Publication Data
US 2015/0329655 A1    Nov. 19, 2015

Related U.S. Application Data

(60) Provisional application No. 61/993,633, filed on May 15, 2014.

(51) Int. Cl.
| | | |
|---|---|---|
| C08C 3/00 | (2006.01) |
| C08F 136/06 | (2006.01) |
| C08L 9/00 | (2006.01) |
| C07C 255/61 | (2006.01) |
| C08C 19/22 | (2006.01) |
| C08F 8/30 | (2006.01) |
| C08F 36/00 | (2006.01) |

(52) U.S. Cl.
CPC .......... C08F 136/06 (2013.01); C07C 255/61 (2013.01); C08C 3/00 (2013.01); C08C 19/22 (2013.01); C08F 8/30 (2013.01); C08F 36/00 (2013.01); C08L 9/00 (2013.01)

(58) Field of Classification Search
CPC .......... C08F 8/30; C08F 36/00; C08F 136/06; C08C 3/00; C08C 19/22; C08L 9/00
See application file for complete search history.

(56) References Cited

U.S. PATENT DOCUMENTS

| | | | |
|---|---|---|---|
| 2006/0106017 A1 | 5/2006 | Jeong et al. | |
| 2008/0146745 A1 | 6/2008 | Luo et al. | |
| 2010/0280217 A1* | 11/2010 | Luo | B60C 1/00 528/319 |

* cited by examiner

*Primary Examiner* — Peter D. Mulcahy
(74) *Attorney, Agent, or Firm* — Meredith E. Hooker; Arthur M. Reginelli

(57) ABSTRACT

A method for preparing a functionalized polymer, the method comprising the steps of: (i) polymerizing monomer to form a reactive polymer, and (ii) reacting the reactive polymer with a protected oxime compound containing a cyano group.

22 Claims, 1 Drawing Sheet

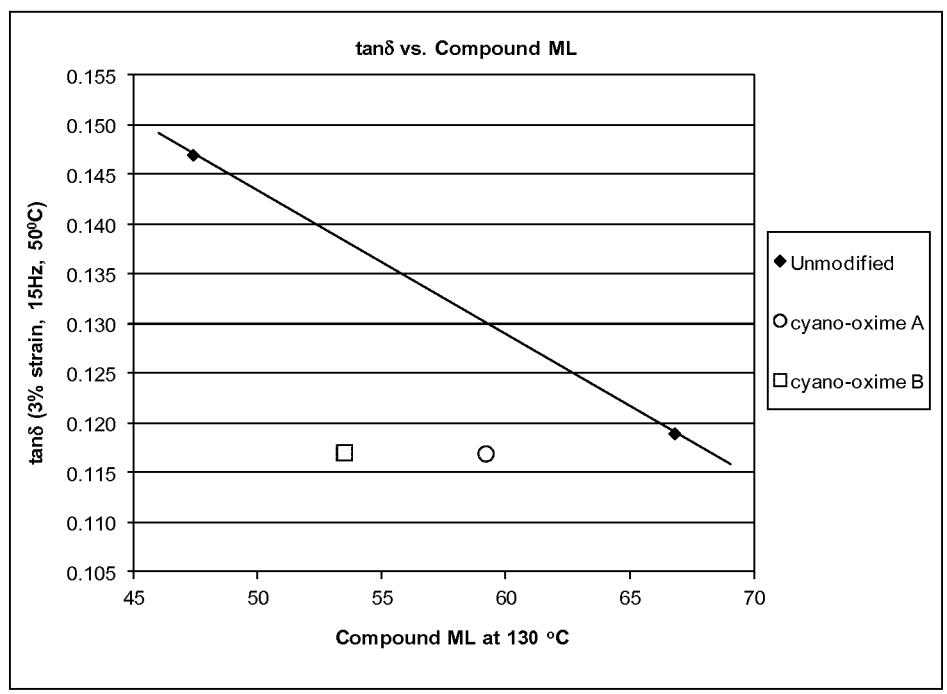

POLYMERS FUNCTIONALIZED WITH PROTECTED OXIME COMPOUNDS CONTAINING A CYANO GROUP

This application claims the benefit of U.S. Provisional Application Ser. No. 61/993,633, filed on May 15, 2015, which is incorporated herein by reference.

FIELD OF THE INVENTION

One or more embodiments of the present invention relate to polymers functionalized with protected oxime compounds containing a cyano group.

BACKGROUND OF THE INVENTION

In the art of manufacturing tires, it is desirable to employ rubber vulcanizates that demonstrate reduced hysteresis, i.e., less loss of mechanical energy to heat. For example, rubber vulcanizates that show reduced hysteresis are advantageously employed in tire components, such as sidewalls and treads, to yield tires having desirably low rolling resistance. The hysteresis of a rubber vulcanizate is often attributed to the free polymer chain ends within a crosslinked rubber network, as well as the dissociation of filler agglomerates.

Functionalized polymers have been employed to reduce the hysteresis of rubber vulcanizates. The functional group of the functionalized polymer may reduce the number of free polymer chain ends via interaction with filler particles. Also, the functional group may reduce filler agglomeration. Nevertheless, whether a particular functional group imparted to a polymer can reduce hysteresis is often unpredictable.

Functionalized polymers may be prepared by post-polymerization treatment of reactive polymers with certain functionalizing agents. However, whether a reactive polymer can be functionalized by treatment with a particular functionalizing agent can be unpredictable. For example, functionalizing agents that work for one type of polymer do not necessarily work for another type of polymer, and vice versa.

Lanthanide-based catalyst systems are known to be useful for polymerizing conjugated diene monomer to form polydienes having a high content of cis-1,4-linkage. The resulting cis-1,4-polydienes may display pseudo-living characteristics in that, upon completion of the polymerization, some of the polymer chains possess reactive ends that can react with certain functionalizing agents to yield functionalized cis-1,4-polydienes.

The cis-1,4-polydienes produced with lanthanide-based catalyst systems typically have a linear backbone, which is believed to provide better tensile properties, higher abrasion resistance, lower hysteresis, and better fatigue resistance as compared to the cis-1,4-polydienes prepared with other catalyst systems such as titanium-, cobalt-, and nickel-based catalyst systems. Therefore, the cis-1,4-polydienes made with lanthanide-based catalysts are particularly suitable for use in tire components such as sidewalls and treads.

Anionic initiators are known to be useful for the polymerization of conjugated diene monomer to form polydienes having a combination of 1,2-, cis-1,4- and trans-1,4-linkages. Anionic initiators are also useful for the copolymerization of conjugated diene monomer with vinyl-substituted aromatic compounds. The polymers prepared with anionic initiators may display living characteristics in that, upon completion of the polymerization, the polymer chains possess living ends that are capable of reacting with additional monomer for further chain growth or reacting with certain functionalizing agents to give functionalized polymers.

Because functionalized polymers are advantageous, especially in the manufacture of tires, there exists a need to develop new functionalized polymers that give reduced hysteresis.

SUMMARY OF THE INVENTION

One or more embodiments of the present invention provides a method for preparing a functionalized polymer, the method comprising the steps of: (i) polymerizing monomer to form a reactive polymer, and (ii) reacting the reactive polymer with a protected oxime compound containing a cyano group.

Other embodiments of the present invention provide a method for preparing a functionalized polymer, the method comprising the steps of: (i) polymerizing conjugated diene monomer, and optionally monomer copolymerizable therewith, to form a polymer having a reactive chain end; and (ii) reacting the reactive chain end of the polymer with a protected oxime compound containing a cyano group.

Other embodiments of the present invention provide a functionalized polymer prepared by the steps of: (i) polymerizing conjugated diene monomer, and optionally monomer copolymerizable therewith, to form a polymer having a reactive chain end; and (ii) reacting the reactive chain end of the polymer with a protected oxime compound containing a cyano group.

Other embodiments of the present invention provide an oxime compound containing a cyano group defined by the formula I:

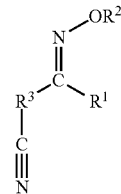

where $R^1$ is a hydrogen atom or monovalent organic group, $R^2$ is a monovalent organic group, and $R^3$ is a bond or a divalent organic group, or where $R^1$ and $R^3$ join to form a trivalent organic group.

BRIEF DESCRIPTION OF THE DRAWINGS

The FIGURE is a graphical plot of hysteresis loss (tan δ) versus Mooney viscosity ($ML_{1+4}$ at 130° C.) for vulcanizates prepared from functionalized cis-1,4-polybutadiene prepared according to one or more embodiments of the present invention as compared to vulcanizates prepared from unfunctionalized cis-1,4-polybutadiene.

DETAILED DESCRIPTION OF ILLUSTRATIVE EMBODIMENTS

According to one or more embodiments of the present invention, a reactive polymer is prepared by polymerizing conjugated diene monomer and optionally monomer copolymerizable therewith, and this reactive polymer is then functionalized by reaction with a protected oxime compound containing a cyano group. The resultant functionalized polymers can be used in the manufacture of tire components. In one or more embodiments, the resultant functionalized polymers provide tire components that exhibit advantageously low hysteresis.

Examples of conjugated diene monomer include 1,3-butadiene, isoprene, 1,3-pentadiene, 1,3-hexadiene, 2,3-dimethyl-1,3-butadiene, 2-ethyl-1,3-butadiene, 2-methyl-1,3-pentadiene, 3-methyl-1,3-pentadiene, 4-methyl-1,3-pentadiene, and 2,4-hexadiene. Mixtures of two or more conjugated dienes may also be utilized in copolymerization.

Examples of monomer copolymerizable with conjugated diene monomer include vinyl-substituted aromatic compounds such as styrene, p-methylstyrene, α-methylstyrene, and vinylnaphthalene.

In one or more embodiments, the reactive polymer is prepared by coordination polymerization, wherein monomer is polymerized by using a coordination catalyst system. The key mechanistic features of coordination polymerization have been discussed in books (e.g., Kuran, W., *Principles of Coordination Polymerization*; John Wiley & Sons: New York, 2001) and review articles (e.g., Mulhaupt, R., Macromolecular Chemistry and Physics 2003, volume 204, pages 289-327). Coordination catalysts are believed to initiate the polymerization of monomer by a mechanism that involves the coordination or complexation of monomer to an active metal center prior to the insertion of monomer into a growing polymer chain. An advantageous feature of coordination catalysts is their ability to provide stereochemical control of polymerizations and thereby produce stereoregular polymers. As is known in the art, there are numerous methods for creating coordination catalysts, but all methods eventually generate an active intermediate that is capable of coordinating with monomer and inserting monomer into a covalent bond between an active metal center and a growing polymer chain. The coordination polymerization of conjugated dienes is believed to proceed via π-allyl complexes as intermediates. Coordination catalysts can be one-, two-, three- or multi-component systems. In one or more embodiments, a coordination catalyst may be formed by combining a heavy metal compound (e.g., a transition metal compound or a lanthanide-containing compound), an alkylating agent (e.g., an organoaluminum compound), and optionally other co-catalyst components (e.g., a Lewis acid or a Lewis base). In one or more embodiments, the heavy metal compound may be referred to as a coordinating metal compound.

Various procedures can be used to prepare coordination catalysts. In one or more embodiments, a coordination catalyst may be formed in situ by separately adding the catalyst components to the monomer to be polymerized in either a stepwise or simultaneous manner. In other embodiments, a coordination catalyst may be preformed. That is, the catalyst components are pre-mixed outside the polymerization system either in the absence of any monomer or in the presence of a small amount of monomer. The resulting preformed catalyst composition may be aged, if desired, and then added to the monomer that is to be polymerized.

Useful coordination catalyst systems include lanthanide-based catalyst systems. These catalyst systems may advantageously produce cis-1,4-polydienes that, prior to quenching, have reactive chain ends and may be referred to as pseudo-living polymers. While other coordination catalyst systems may also be employed, lanthanide-based catalysts have been found to be particularly advantageous, and therefore, without limiting the scope of the present invention, will be discussed in greater detail.

Practice of the present invention is not necessarily limited by the selection of any particular lanthanide-based catalyst system. In one or more embodiments, the catalyst systems employed include (a) a lanthanide-containing compound, (b) an alkylating agent, and (c) a halogen source. In other embodiments, a compound containing a non-coordinating anion or a non-coordinating anion precursor can be employed in lieu of a halogen source. In these or other embodiments, other organometallic compounds, Lewis bases, and/or catalyst modifiers can be employed in addition to the ingredients or components set forth above. For example, in one embodiment, a nickel-containing compound can be employed as a molecular weight regulator as disclosed in U.S. Pat. No. 6,699,813, which is incorporated herein by reference.

As mentioned above, the lanthanide-based catalyst systems employed in the present invention can include a lanthanide-containing compound. Lanthanide-containing compounds useful in the present invention are those compounds that include at least one atom of lanthanum, neodymium, cerium, praseodymium, promethium, samarium, europium, gadolinium, terbium, dysprosium, holmium, erbium, thulium, ytterbium, lutetium, and didymium. In one embodiment, these compounds can include neodymium, lanthanum, samarium, or didymium. As used herein, the term "didymium" shall denote a commercial mixture of rare-earth elements obtained from monazite sand. In addition, the lanthanide-containing compounds useful in the present invention can be in the form of elemental lanthanide.

The lanthanide atom in the lanthanide-containing compounds can be in various oxidation states including, but not limited to, the 0, +2, +3, and +4 oxidation states. In one embodiment, a trivalent lanthanide-containing compound, where the lanthanide atom is in the +3 oxidation state, can be employed. Suitable lanthanide-containing compounds include, but are not limited to, lanthanide carboxylates, lanthanide organophosphates, lanthanide organophosphonates, lanthanide organophosphinates, lanthanide carbamates, lanthanide dithiocarbamates, lanthanide xanthates, lanthanide β-diketonates, lanthanide alkoxides or aryloxides, lanthanide halides, lanthanide pseudo-halides, lanthanide oxyhalides, and organolanthanide compounds.

In one or more embodiments, the lanthanide-containing compounds can be soluble in hydrocarbon solvents such as aromatic hydrocarbons, aliphatic hydrocarbons, or cycloaliphatic hydrocarbons. Hydrocarbon-insoluble lanthanide-containing compounds, however, may also be useful in the present invention, as they can be suspended in the polymerization medium to form the catalytically active species.

For ease of illustration, further discussion of useful lanthanide-containing compounds will focus on neodymium compounds, although those skilled in the art will be able to select similar compounds that are based upon other lanthanide metals.

Suitable neodymium carboxylates include, but are not limited to, neodymium formate, neodymium acetate, neodymium acrylate, neodymium methacrylate, neodymium valerate, neodymium gluconate, neodymium citrate, neodymium fumarate, neodymium lactate, neodymium maleate, neodymium oxalate, neodymium 2-ethylhexanoate, neodymium neodecanoate (a.k.a., neodymium versatate), neodymium naphthenate, neodymium stearate, neodymium oleate, neodymium benzoate, and neodymium picolinate.

Suitable neodymium organophosphates include, but are not limited to, neodymium dibutyl phosphate, neodymium dipentyl phosphate, neodymium dihexyl phosphate, neodymium diheptyl phosphate, neodymium dioctyl phosphate, neodymium bis(1-methylheptyl) phosphate, neodymium bis(2-ethylhexyl) phosphate, neodymium didecyl phosphate, neodymium didodecyl phosphate, neodymium dioctadecyl phosphate, neodymium dioleyl phosphate, neodymium diphenyl phosphate, neodymium bis(p-nonylphenyl) phosphate, neodymium butyl (2-ethylhexyl) phosphate, neodymium (1-methylheptyl) (2-ethylhexyl) phosphate, and neodymium (2-ethylhexyl) (p-nonylphenyl) phosphate.

Suitable neodymium organophosphonates include, but are not limited to, neodymium butyl phosphonate, neodymium pentyl phosphonate, neodymium hexyl phosphonate, neodymium heptyl phosphonate, neodymium octyl phosphonate, neodymium (1-methylheptyl) phosphonate, neodymium (2-ethylhexyl) phosphonate, neodymium decyl phosphonate, neodymium dodecyl phosphonate, neodymium octadecyl phosphonate, neodymium oleyl phosphonate, neodymium phenyl phosphonate, neodymium (p-nonylphenyl) phosphonate, neodymium butyl butylphosphonate, neodymium pentyl pentylphosphonate, neodymium hexyl hexylphosphonate, neodymium heptyl heptylphosphonate, neodymium octyl octylphosphonate, neodymium (1-methylheptyl) (1-methylheptyl)phosphonate, neodymium (2-ethylhexyl) (2-ethylhexyl)phosphonate, neodymium decyl decylphosphonate, neodymium dodecyl dodecylphosphonate, neodymium octadecyl octadecylphosphonate, neodymium oleyl oleylphosphonate, neodymium phenyl phenylphosphonate, neodymium (p-nonylphenyl) (p-nonylphenyl)phosphonate, neodymium butyl (2-ethylhexyl)phosphonate, neodymium (2-ethylhexyl) butylphosphonate, neodymium (1-methylheptyl) (2-ethylhexyl)phosphonate, neodymium (2-ethylhexyl) (1-methylheptyl)phosphonate, neodymium (2-ethylhexyl) (p-nonylphenyl)phosphonate, and neodymium (p-nonylphenyl) (2-ethylhexyl) phosphonate.

Suitable neodymium organophosphinates include, but are not limited to, neodymium butylphosphinate, neodymium pentylphosphinate, neodymium hexylphosphinate, neodymium heptylphosphinate, neodymium octylphosphinate, neodymium (1-methylheptyl)phosphinate, neodymium (2-ethylhexyl)phosphinate, neodymium decylphosphinate, neodymium dodecylphosphinate, neodymium octadecylphosphinate, neodymium oleylphosphinate, neodymium phenylphosphinate, neodymium (p-nonylphenyephosphinate, neodymium dibutylphosphinate, neodymium dipentylphosphinate, neodymium dihexylphosphinate, neodymium diheptylphosphinate, neodymium dioctylphosphinate, neodymium bis(1-methylheptyl)phosphinate, neodymium bis (2-ethylhexyl)phosphinate, neodymium didecylphosphinate, neodymium didodecylphosphinate, neodymium dioctadecylphosphinate, neodymium dioleylphosphinate, neodymium diphenylphosphinate, neodymium bis(p-nonylphenyl) phosphinate, neodymium butyl (2-ethylhexyl) phosphinate, neodymium (1-methylheptyl)(2-ethylhexyl)phosphinate, and neodymium (2-ethylhexyl)(p-nonylphenyl) phosphinate.

Suitable neodymium carbamates include, but are not limited to, neodymium dimethylcarbamate, neodymium diethylcarbamate, neodymium diisopropylcarbamate, neodymium dibutylcarbamate, and neodymium dibenzylcarbamate.

Suitable neodymium dithiocarbamates include, but are not limited to, neodymium dimethyldithiocarbamate, neodymium diethyldithiocarbamate, neodymium diisopropyldithiocarbamate, neodymium dibutyldithiocarbamate, and neodymium dibenzyldithiocarbamate.

Suitable neodymium xanthates include, but are not limited to, neodymium methylxanthate, neodymium ethylxanthate, neodymium isopropylxanthate, neodymium butylxanthate, and neodymium benzylxanthate.

Suitable neodymium β-diketonates include, but are not limited to, neodymium acetylacetonate, neodymium trifluoroacetylacetonate, neodymium hexafluoroacetylacetonate, neodymium benzoylacetonate, and neodymium 2,2,6,6-tetramethyl-3,5-heptanedionate.

Suitable neodymium alkoxides or aryloxides include, but are not limited to, neodymium methoxide, neodymium ethoxide, neodymium isopropoxide, neodymium 2-ethylhexoxide, neodymium phenoxide, neodymium nonylphenoxide, and neodymium naphthoxide.

Suitable neodymium halides include, but are not limited to, neodymium fluoride, neodymium chloride, neodymium bromide, and neodymium iodide. Suitable neodymium pseudo-halides include, but are not limited to, neodymium cyanide, neodymium cyanate, neodymium thiocyanate, neodymium azide, and neodymium ferrocyanide. Suitable neodymium oxyhalides include, but are not limited to, neodymium oxyfluoride, neodymium oxychloride, and neodymium oxybromide. A Lewis base, such as tetrahydrofuran ("THF"), may be employed as an aid for solubilizing this class of neodymium compounds in inert organic solvents. Where lanthanide halides, lanthanide oxyhalides, or other lanthanide-containing compounds containing a halogen atom are employed, the lanthanide-containing compound may optionally also provide all or part of the halogen source in the lanthanide-based catalyst system.

As used herein, the term organolanthanide compound refers to any lanthanide-containing compound containing at least one lanthanide-carbon bond. These compounds are predominantly, though not exclusively, those containing cyclopentadienyl ("Cp"), substituted cyclopentadienyl, allyl, and substituted allyl ligands. Suitable organolanthanide compounds include, but are not limited to, $Cp_3Ln$, $Cp_2LnR$, $Cp_2LnCl$, $CpLnCl_2$, $CpLn(cyclooctatetraene)$, $(C_5Me_5)_2LnR$, $LnR_3$, $Ln(allyl)_3$, and $Ln(allyl)_2Cl$, where Ln represents a lanthanide atom, and R represents a hydrocarbyl group. In one or more embodiments, hydrocarbyl groups useful in the present invention may contain heteroatoms such as, for example, nitrogen, oxygen, boron, silicon, sulfur, and phosphorus atoms.

As mentioned above, the lanthanide-based catalyst systems employed in the present invention can include an alkylating agent. In one or more embodiments, alkylating agents, which may also be referred to as hydrocarbylating agents, include organometallic compounds that can transfer one or more hydrocarbyl groups to another metal. Generally, these agents include organometallic compounds of electropositive metals such as Groups 1, 2, and 3 metals (Groups IA, IIA, and IIIA metals). Alkylating agents useful in the present invention include, but are not limited to, organoaluminum and organomagnesium compounds. As used herein, the term organoaluminum compound refers to any aluminum compound containing at least one aluminum-carbon bond. In one or more embodiments, organoaluminum compounds that are soluble in a hydrocarbon solvent can be employed. As used herein, the term organomagnesium compound refers to any magnesium compound that contains at least one magnesium-carbon bond. In one or more embodiments, organomagnesium compounds that are soluble in a hydrocarbon can be employed. As will be described in more detail below, several species of suitable alkylating agents can be in the form of a halide. Where the alkylating agent includes a halogen atom, the alkylating agent may also serve as all or part of the halogen source in the above-mentioned catalyst system.

In one or more embodiments, organoaluminum compounds that can be utilized in the lanthanide-based catalyst system include those represented by the general formula $AlR_nX_{3-n}$, where each R independently can be a monovalent organic group that is attached to the aluminum atom via a carbon atom, where each X independently can be a hydrogen atom, a halogen atom, a carboxylate group, an alkoxide group, or an aryloxide group, and where n can be an integer in the range of from 1 to 3. In one or more embodiments, each R independently can be a hydrocarbyl group such as, for example, alkyl, cycloalkyl, substituted cycloalkyl, alkenyl, cycloalkenyl, substituted cycloalkenyl, aryl, substituted aryl, aralkyl, alkaryl, allyl, and alkynyl groups, with each group containing in the range of from 1 carbon atom, or the appropriate minimum number of carbon atoms to form the group, up to about 20 carbon atoms. These hydrocarbyl groups may contain heteroatoms including, but not limited to, nitrogen, oxygen, boron, silicon, sulfur, and phosphorus atoms.

Types of the organoaluminum compounds that are represented by the general formula $AlR_nX_{3-n}$ include, but are not limited to, trihydrocarbylaluminum, dihydrocarbylaluminum hydride, hydrocarbylaluminum dihydride, dihydrocarbylaluminum carboxylate, hydrocarbylaluminum bis(carboxylate), dihydrocarbylaluminum alkoxide, hydrocarbylaluminum dialkoxide, dihydrocarbylaluminum halide, hydrocarbylaluminum dihalide, dihydrocarbylaluminum aryloxide, and hydrocarbylaluminum diaryloxide compounds. In one embodiment, the alkylating agent can comprise trihydrocarbylaluminum, dihydrocarbylaluminum hydride, and/or hydrocarbylaluminum dihydride compounds. In one embodiment, when the alkylating agent includes an organoaluminum hydride compound, the abovementioned halogen source can be provided by a tin halide, as disclosed in U.S. Pat. No. 7,008,899, which is incorporated herein by reference in its entirety.

Suitable trihydrocarbylaluminum compounds include, but are not limited to, trimethylaluminum, triethylaluminum, triisobutylaluminum, tri-n-propylaluminum, triisopropylaluminum, tri-n-butylaluminum, tri-t-butylaluminum, tri-n-pentylaluminumi, trineopentylaluminum, tri-n-hexylaluminum, tri-n-octylaluminum, tris(2-ethylhexyl) aluminum, tricyclohexylaluminum, tris(1-methylcyclopentyl) aluminum, triphenylaluminum, tri-p-tolylaluminum, tris(2,6-dimethylphenyl)aluminum, tribenzylaluminum, diethylphenylaluminum, diethyl-p-tolylaluminum, diethylbenzylaluminum, ethyldiphenylaluminum, ethyldi-p-tolylaluminum, and ethyldibenzylaluminum.

Suitable dihydrocarbylaluminum hydride compounds include, but are not limited to, diethylaluminum hydride, di-n-propylaluminum hydride, diisopropylaluminum hydride, di-n-butylaluminum hydride, diisobutylaluminum hydride, di-n-octylaluminum hydride, diphenylaluminum hydride, di-p-tolylaluminum hydride, dibenzylaluminum hydride, phenylethylaluminum hydride, phenyl-n-propylaluminum hydride, phenylisopropylaluminum hydride, phenyl-n-butylaluminum hydride, phenylisobutylaluminum hydride, phenyl-n-octylaluminum hydride, p-tolylethylaluminum hydride, p-tolyl-n-propylaluminum hydride, p-tolylisopropylaluminum hydride, p-tolyl-n-butylaluminum hydride, p-tolylisobutylaluminum hydride, p-tolyl-n-octylaluminum hydride, benzylethylaluminum hydride, benzyl-n-propylaluminum hydride, benzylisopropylaluminum hydride, benzyl-n-butylaluminum hydride, benzylisobutylaluminum hydride, and benzyl-n-octylaluminum hydride.

Suitable hydrocarbylaluminum dihydrides include, but are not limited to, ethylaluminum dihydride, n-propylaluminum dihydride, isopropylaluminum dihydride, n-butylaluminum dihydride, isobutylaluminum dihydride, and n-octylaluminum dihydride.

Suitable dihydrocarbylaluminum halide compounds include, but are not limited to, diethylaluminum chloride, di-n-propylaluminum chloride, diisopropylaluminum chloride, di-n-butylaluminum chloride, diisobutylaluminum chloride, di-n-octylaluminum chloride, diphenylaluminum chloride, di-p-tolylaluminum chloride, dibenzylaluminum chloride, phenylethylaluminum chloride, phenyl-n-propylaluminum chloride, phenylisopropylaluminum chloride, phenyl-n-butylaluminum chloride, phenylisobutylaluminum chloride, phenyl-n-octylaluminum chloride, p-tolylethylaluminum chloride, p-tolyl-n-propylaluminum chloride, p-tolylisopropylaluminum chloride, p-tolyl-n-butylaluminum chloride, p-tolylisobutylaluminum chloride, p-tolyl-n-octylaluminum chloride, benzylethylaluminum chloride, benzyl-n-propylaluminum chloride, benzylisopropylaluminum chloride, benzyl-n-butylaluminum chloride, benzylisobutylaluminum chloride, and benzyl-n-octylaluminum chloride.

Suitable hydrocarbylaluminum dihalide compounds include, but are not limited to, ethylaluminum dichloride, n-propylaluminum dichloride, isopropylaluminum dichloride, n-butylaluminum dichloride, isobutylaluminum dichloride, and n-octylaluminum dichloride.

Other organoaluminum compounds useful as alkylating agents that may be represented by the general formula $AlR_nX_{3-n}$ include, but are not limited to, dimethylaluminum hexanoate, diethylaluminum octoate, diisobutylaluminum 2-ethylhexanoate, dimethylaluminum neodecanoate, diethylaluminum stearate, diisobutylaluminum oleate, methylaluminum bis(hexanoate), ethylaluminum bis(octoate), isobutylaluminum bis(2-ethylhexanoate), methylaluminum bis(neodecanoate), ethylaluminum bis(stearate), isobutylaluminum bis(oleate), dimethylaluminum methoxide, diethylaluminum methoxide, diisobutylaluminum methoxide, dimethylaluminum ethoxide, diethylaluminum ethoxide, diisobutylaluminum ethoxide, dimethylaluminum phenoxide, diethylaluminum phenoxide, diisobutylaluminum phenoxide, methylaluminum dimethoxide, ethylaluminum dimethoxide, isobutylaluminum dimethoxide, methylaluminum diethoxide, ethylaluminum diethoxide, isobutylaluminum diethoxide, methylaluminum diphenoxide, ethylaluminum diphenoxide, and isobutylaluminum diphenoxide.

Another class of organoaluminum compounds suitable for use as an alkylating agent in the lanthanide-based catalyst system is aluminoxanes. Aluminoxanes can comprise oligomeric linear aluminoxanes, which can be represented by the general formula:

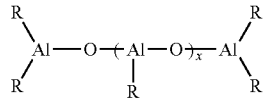

and oligomeric cyclic aluminoxanes, which can be represented by the general formula:

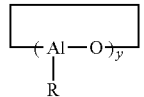

where x can be an integer in the range of from 1 to about 100, or about 10 to about 50; y can be an integer in the range of from 2 to about 100, or about 3 to about 20; and where each R independently can be a monovalent organic group that is attached to the aluminum atom via a carbon atom. In one embodiment, each R independently can be a hydrocarbyl group including, but not limited to, alkyl, cycloalkyl, substituted cycloalkyl, alkenyl, cycloalkenyl, substituted cycloalkenyl, aryl, substituted aryl, aralkyl, alkaryl, allyl, and alkynyl groups, with each group containing in the range of from 1 carbon atom, or the appropriate minimum number of carbon atoms to form the group, up to about 20 carbon atoms. These hydrocarbyl groups may also contain heteroatoms including, but not limited to, nitrogen, oxygen, boron, silicon, sulfur, and phosphorus atoms. It should be noted that the number of moles of the aluminoxane as used in this application refers to the number of moles of the aluminum atoms rather than the number of moles of the oligomeric aluminoxane molecules. This convention is commonly employed in the art of catalyst systems utilizing aluminoxanes.

Aluminoxanes can be prepared by reacting trihydrocarbylaluminum compounds with water. This reaction can be performed according to known methods, such as, for example, (1) a method in which the trihydrocarbylaluminum compound is dissolved in an organic solvent and then contacted with water, (2) a method in which the trihydrocarbylaluminum compound is reacted with water of crystallization contained in, for example, metal salts, or water adsorbed in inorganic or organic compounds, or (3) a method in which the trihydrocarbylaluminum compound is reacted with water in the presence of the monomer or monomer solution that is to be polymerized.

Suitable aluminoxane compounds include, but are not limited to, methylaluminoxane ("MAO"), modified methylaluminoxane ("MMAO"), ethylaluminoxane, n-propylaluminoxane, isopropylaluminoxane, butylaluminoxane, isobutylaluminoxane, n-pentylaluminoxane, neopentylaluminoxane, n-hexylaluminoxane, n-octylaluminoxane, 2-ethylhexylaluminoxane, cyclohexylaluminoxane, 1-methylcyclopentylaluminoxane, phenylaluminoxane, and 2,6-dimethylphenylaluminoxane. Modified methylaluminoxane can be formed by substituting about 20 to 80 percent of the methyl groups of methylaluminoxane with $C_2$ to $C_{12}$ hydrocarbyl groups, preferably with isobutyl groups, by using techniques known to those skilled in the art.

In one or more embodiments, aluminoxanes can be used alone or in combination with other organoaluminum compounds. In one embodiment, methylaluminoxane and at least one other organoaluminum compound (e.g., $AlR_nX_{3-n}$), such as diisobutyl aluminum hydride, can be employed in combination. U.S. Publication No. 2008/0182954, which is incorporated herein by reference in its entirety, provides other examples where aluminoxanes and organoaluminum compounds can be employed in combination.

As mentioned above, alkylating agents useful in the lanthanide-based catalyst system can include organomagnesium compounds. In one or more embodiments, organomagnesium compounds that can be utilized include those represented by the general formula $MgR_2$, where each R independently can be a monovalent organic group that is attached to the magnesium atom via a carbon atom. In one or more embodiments, each R independently can be a hydrocarbyl group including, but not limited to, alkyl, cycloalkyl, substituted cycloalkyl, alkenyl, cycloalkenyl, substituted cycloalkenyl, aryl, allyl, substituted aryl, aralkyl, alkaryl, and alkynyl groups, with each group containing in the range of from 1 carbon atom, or the appropriate minimum number of carbon atoms to form the group, up to about 20 carbon atoms. These hydrocarbyl groups may also contain heteroatoms including, but not limited to, nitrogen, oxygen, silicon, sulfur, and phosphorus atoms.

Suitable organomagnesium compounds that may be represented by the general formula $MgR_2$ include, but are not limited to, diethylmagnesium, di-n-propylmagnesium, diisopropylmagnesium, dibutylmagnesium, dihexylmagnesium, diphenylmagnesium, and dibenzylmagnesium.

Another class of organomagnesium compounds that can be utilized as an alkylating agent may be represented by the general formula RMgX, where R can be a monovalent organic group that is attached to the magnesium atom via a carbon atom, and X can be a hydrogen atom, a halogen atom, a carboxylate group, an alkoxide group, or an aryloxide group. Where the alkylating agent is an organomagnesium compound that includes a halogen atom, the organomagnesium compound can serve as both the alkylating agent and at least a portion of the halogen source in the catalyst systems. In one or more embodiments, R can be a hydrocarbyl group including, but not limited to, alkyl, cycloalkyl, substituted cycloalkyl, alkenyl, cycloalkenyl, substituted cycloalkenyl, aryl, allyl, substituted aryl, aralkyl, alkaryl, and alkynyl groups, with each group containing in the range of from 1 carbon atom, or the appropriate minimum number of carbon atoms to form the group, up to about 20 carbon atoms. These hydrocarbyl groups may also contain heteroatoms including, but not limited to, nitrogen, oxygen, boron, silicon, sulfur, and phosphorus atoms. In one embodiment, X can be a carboxylate group, an alkoxide group, or an aryloxide group, with each group containing in the range of from 1 to about 20 carbon atoms.

Types of organomagnesium compounds that may be represented by the general formula RMgX include, but are not limited to, hydrocarbylmagnesium hydride, hydrocarbylmagnesium halide, hydrocarbylmagnesium carboxylate, hydrocarbylmagnesium alkoxide, and hydrocarbylmagnesium aryloxide.

Suitable organomagnesium compounds that may be represented by the general formula RMgX include, but are not limited to, methylmagnesium hydride, ethylmagnesium hydride, butylmagnesium hydride, hexylmagnesium hydride, phenylmagnesium hydride, benzylmagnesium hydride, methylmagnesium chloride, ethylmagnesium chloride, butylmagnesium chloride, hexylmagnesium chloride, phenylmagnesium chloride, benzylmagnesium chloride, methylmagnesium bromide, ethylmagnesium bromide, butylmagnesium bromide, hexylmagnesium bromide, phenylmagnesium bromide, benzylmagnesium bromide, methylmagnesium hexanoate, ethylmagnesium hexanoate, butylmagnesium hexanoate, hexylmagnesium hexanoate, phenylmagnesium hexanoate, benzylmagnesium hexanoate, methylmagnesium ethoxide, ethylmagnesium ethoxide, butylmagnesium ethoxide, hexylmagnesium ethoxide, phenylmagnesium ethoxide, benzylmagnesium ethoxide, methylmagnesium phenoxide, ethylmagnesium phenoxide, butylmagnesium phenoxide, hexylmagnesium phenoxide, phenylmagnesium phenoxide, and benzylmagnesium phenoxide.

As mentioned above, the lanthanide-based catalyst systems employed in the present invention can include a halogen source. As used herein, the term halogen source refers to any substance including at least one halogen atom. In one or more embodiments, at least a portion of the halogen source can be provided by either of the above-described lanthanide-containing compound and/or the above-described alkylating agent, when those compounds contain at least one halogen atom. In other words, the lanthanide-containing compound can serve as both the lanthanide-containing compound and at least a portion of the halogen source. Similarly, the alkylating agent can serve as both the alkylating agent and at least a portion of the halogen source.

In another embodiment, at least a portion of the halogen source can be present in the catalyst systems in the form of a separate and distinct halogen-containing compound. Various compounds, or mixtures thereof, that contain one or more halogen atoms can be employed as the halogen source. Examples of halogen atoms include, but are not limited to, fluorine, chlorine, bromine, and iodine. A combination of two or more halogen atoms can also be utilized. Halogen-containing compounds that are soluble in a hydrocarbon solvent are suitable for use in the present invention. Hydrocarbon-insoluble halogen-containing compounds, however, can be suspended in a polymerization system to form the catalytically active species, and are therefore also useful.

Useful types of halogen-containing compounds that can be employed include, but are not limited to, elemental halogens, mixed halogens, hydrogen halides, organic halides, inorganic halides, metallic halides, and organometallic halides.

Suitable elemental halogens include, but are not limited to, fluorine, chlorine, bromine, and iodine. Some specific examples of suitable mixed halogens include iodine monochloride, iodine monobromide, iodine trichloride, and iodine pentafluoride.

Suitable hydrogen halides include, but are not limited to, hydrogen fluoride, hydrogen chloride, hydrogen bromide, and hydrogen iodide.

Suitable organic halides include, but are not limited to, t-butyl chloride, t-butyl bromide, allyl chloride, allyl bromide, benzyl chloride, benzyl bromide, chloro-di-phenylmethane, bromo-di-phenylmethane, triphenylmethyl chloride, triphenylmethyl bromide, benzylidene chloride, benzylidene bromide, methyltrichlorosilane, phenyltrichlorosilane, dimethyldichlorosilane, diphenyldichlorosilane, trimethylchlorosilane, benzoyl chloride, benzoyl bromide, propionyl chloride, propionyl bromide, methyl chloroformate, and methyl bromoformate.

Suitable inorganic halides include, but are not limited to, phosphorus trichloride, phosphorus tribromide, phosphorus pentachloride, phosphorus oxychloride, phosphorus oxybromide, boron trifluoride, boron trichloride, boron tribromide, silicon tetrafluoride, silicon tetrachloride, silicon tetrabromide, silicon tetraiodide, arsenic trichloride, arsenic tribromide, arsenic triiodide, selenium tetrachloride, selenium tetrabromide, tellurium tetrachloride, tellurium tetrabromide, and tellurium tetraiodide.

Suitable metallic halides include, but are not limited to, tin tetrachloride, tin tetrabromide, aluminum trichloride, aluminum tribromide, antimony trichloride, antimony pentachloride, antimony tribromide, aluminum triiodide, aluminum trifluoride, gallium trichloride, gallium tribromide, gallium triiodide, gallium trifluoride, indium trichloride, indium tribromide, indium triiodide, indium trifluoride, titanium tetrachloride, titanium tetrabromide, titanium tetraiodide, zinc dichloride, zinc dibromide, zinc diiodide, and zinc difluoride.

Suitable organometallic halides include, but are not limited to, dimethylaluminum chloride, diethylaluminum chloride, dimethylaluminum bromide, diethylaluminum bromide, dimethylaluminum fluoride, diethylaluminum fluoride, methylaluminum dichloride, ethylaluminum dichloride, methylaluminum dibromide, ethylaluminum dibromide, methylaluminum difluoride, ethylaluminum difluoride, methylaluminum sesquichloride, ethylaluminum sesquichloride, isobutylaluminum sesquichloride, methylmagnesium chloride, methylmagnesium bromide, methylmagnesium iodide, ethylmagnesium chloride, ethylmagnesium bromide, butylmagnesium chloride, butylmagnesium bromide, phenylmagnesium chloride, phenylmagnesium bromide, benzylmagnesium chloride, trimethyltin chloride, trimethyltin bromide, triethyltin chloride, triethyltin bromide, di-t-butyltin dichloride, di-t-butyltin dibromide, dibutyltin dichloride, dibutyltin dibromide, tributyltin chloride, and tributyltin bromide.

In one or more embodiments, the lanthanide-based catalyst systems can comprise a compound containing a non-coordinating anion or a non-coordinating anion precursor. In one or more embodiments, a compound containing a non-coordinating anion, or a non-coordinating anion precursor can be employed in lieu of the above-described halogen source. A non-coordinating anion is a sterically bulky anion that does not form coordinate bonds with, for example, the active center of a catalyst system due to stearic hindrance. Non-coordinating anions useful in the present invention include, but are not limited to, tetraarylborate anions and fluorinated tetraarylborate anions. Compounds containing a non-coordinating anion can also contain a counter cation, such as a carbonium, ammonium, or phosphonium cation. Exemplary counter cations include, but are not limited to, triarylcarbonium cations and N,N-dialkylanilinium cations. Examples of compounds containing a non-coordinating anion and a counter cation include, but are not limited to, triphenylcarbonium tetrakis(pentafluorophenyl) borate, N,N-dimethylanilinium tetrakis(pentafluorophenyl) borate, triphenylcarbonium tetrakis[3,5-bis(trifluoromethyl)phenyl] borate, and N,N-dimethylanilinium tetrakis[3,5-bis(trifluoromethyl)phenyl]borate.

A non-coordinating anion precursor can also be used in this embodiment. A non-coordinating anion precursor is a compound that is able to form a non-coordinating anion under reaction conditions. Useful non-coordinating anion precursors include, but are not limited to, triarylboron compounds, $BR_3$, where R is a strong electron-withdrawing aryl group, such as a pentafluorophenyl or 3,5-bis(trifluoromethyl)phenyl group.

The lanthanide-based catalyst composition used in this invention may be formed by combining or mixing the foregoing catalyst ingredients. Although one or more active catalyst species are believed to result from the combination of the lanthanide-based catalyst ingredients, the degree of interaction or reaction between the various catalyst ingredients or components is not known with any great degree of certainty. Therefore, the term "catalyst composition" has been employed to encompass a simple mixture of the ingredients, a complex of the various ingredients that is caused by physical or chemical forces of attraction, a chemical reaction product of the ingredients, or a combination of the foregoing.

The foregoing lanthanide-based catalyst composition may have high catalytic activity for polymerizing conjugated dienes into cis-1,4-polydienes over a wide range of catalyst concentrations and catalyst ingredient ratios. Several factors may impact the optimum concentration of any one of the catalyst ingredients. For example, because the catalyst ingredients may interact to form an active species, the optimum concentration for any one catalyst ingredient may be dependent upon the concentrations of the other catalyst ingredients.

In one or more embodiments, the molar ratio of the alkylating agent to the lanthanide-containing compound (alkylating agent/Ln) can be varied from about 1:1 to about 1,000:1, in other embodiments from about 2:1 to about 500:1, and in other embodiments from about 5:1 to about 200:1.

In those embodiments where both an aluminoxane and at least one other organoaluminum agent are employed as alkylating agents, the molar ratio of the aluminoxane to the lanthanide-containing compound (aluminoxane/Ln) can be varied from 5:1 to about 1,000:1, in other embodiments from about 10:1 to about 700:1, and in other embodiments from about 20:1 to about 500:1; and the molar ratio of the at least one other organoaluminum compound to the lanthanide-containing compound (Al/Ln) can be varied from about 1:1 to about 200:1, in other embodiments from about 2:1 to about 150:1, and in other embodiments from about 5:1 to about 100:1.

The molar ratio of the halogen-containing compound to the lanthanide-containing compound is best described in terms of the ratio of the moles of halogen atoms in the halogen source to the moles of lanthanide atoms in the lanthanide-containing compound (halogen/Ln). In one or more embodiments, the halogen/Ln molar ratio can be varied from about 0.5:1 to about 20:1, in other embodiments from about 1:1 to about 10:1, and in other embodiments from about 2:1 to about 6:1.

In yet another embodiment, the molar ratio of the non-coordinating anion or non-coordinating anion precursor to the lanthanide-containing compound (An/Ln) may be from about 0.5:1 to about 20:1, in other embodiments from about 0.75:1 to about 10:1, and in other embodiments from about 1:1 to about 6:1.

The lanthanide-based catalyst composition can be formed by various methods.

In one embodiment, the lanthanide-based catalyst composition may be formed in situ by adding the catalyst ingredients to a solution containing monomer and solvent, or to bulk monomer, in either a stepwise or simultaneous manner. In one embodiment, the alkylating agent can be added first, followed by the lanthanide-containing compound, and then followed by the halogen source or by the compound containing a non-coordinating anion or the non-coordinating anion precursor.

In another embodiment, the lanthanide-based catalyst composition may be preformed. That is, the catalyst ingredients are pre-mixed outside the polymerization system either in the absence of any monomer or in the presence of a small amount of at least one conjugated diene monomer at an appropriate temperature, which may be from about −20° C. to about 80° C. The amount of conjugated diene monomer that may be used for preforming the catalyst can range from about 1 to about 500 moles, in other embodiments from about 5 to about 250 moles, and in other embodiments from about 10 to about 100 moles per mole of the lanthanide-containing compound. The resulting catalyst composition may be aged, if desired, prior to being added to the monomer that is to be polymerized.

In yet another embodiment, the lanthanide-based catalyst composition may be formed by using a two-stage procedure. The first stage may involve combining the alkylating agent with the lanthanide-containing compound either in the absence of any monomer or in the presence of a small amount of at least one conjugated diene monomer at an appropriate temperature, which may be from about −20° C. to about 80° C. The amount of monomer employed in the first stage may be similar to that set forth above for pre-forming the catalyst. In the second stage, the mixture formed in the first stage and the halogen source, non-coordinating anion, or non-coordinating anion precursor can be charged in either a stepwise or simultaneous manner to the monomer that is to be polymerized.

In one or more embodiments, the reactive polymer is prepared by anionic polymerization, wherein monomer is polymerized by using an anionic initiator. The key mechanistic features of anionic polymerization have been described in books (e.g., Hsieh, H. L.; Quirk, R. P. Anionic Polymerization: Principles and Practical Applications; Marcel Dekker: New York, 1996) and review articles (e.g., Hadjichristidis, N.; Pitsikalis, M.; Pispas, S.; Iatrou, H.; Chem. Rev. 2001, 101(12), 3747-3792). Anionic initiators may advantageously produce living polymers that, prior to quenching, are capable of reacting with additional monomer for further chain growth or reacting with certain functionalizing agents to give functionalized polymers.

The practice of this invention is not limited by the selection of any particular anionic initiators. In one or more embodiments, the anionic initiator employed is a functional initiator that imparts a functional group at the head of the polymer chain (i.e., the location from which the polymer chain is started). In particular embodiments, the functional group includes one or more heteroatoms (e.g., nitrogen, oxygen, boron, silicon, sulfur, tin, and phosphorus atoms) or heterocyclic groups. In certain embodiments, the functional group reduces the 50° C. hysteresis loss of carbon-black filled vulcanizates prepared from polymers containing the functional group as compared to similar carbon-black filled vulcanizates prepared from polymer that does not include the functional group.

Exemplary anionic initiators include organolithium compounds. In one or more embodiments, organolithium compounds may include heteroatoms. In these or other embodiments, organolithium compounds may include one or more heterocyclic groups.

Types of organolithium compounds include alkyllithium, aryllithium compounds, and cycloalkyllithium compounds. Specific examples of organolithium compounds include ethyllithium, n-propyllithium, isopropyllithium, n-butyllithium, sec-butyllithium, t-butyllithium, n-amyllithium, isoamyllithium, and phenyllithium.

Other anionic initiators include alkylmagnesium halide compounds such as butylmagnesium bromide and phenylmagnesium bromide. Still other anionic initiators include organosodium compounds such as phenylsodium and 2,4,6-trimethylphenylsodium. Also contemplated are those anionic initiators that give rise to di-living polymers, wherein both ends of a polymer chain are living. Examples of such initiators include dilithio initiators such as those prepared by reacting 1,3-diisopropenylbenzene with sec-butyllithium. These and related difunctional initiators are disclosed in U.S. Pat. No. 3,652,516, which is incorporated herein by reference. Radical anionic initiators may also be employed, including those described in U.S. Pat. No. 5,552,483, which is incorporated herein by reference.

In particular embodiments, the organolithium compounds include a cyclic amine-containing compound such as lithiohexamethyleneimine. These and related useful initiators are disclosed in the U.S. Pat. Nos. 5,332,810, 5,329,005, 5,578,542, 5,393,721, 5,698,646, 5,491,230, 5,521,309, 5,496,940, 5,574,109, and 5,786,441, which are incorporated herein by reference. In other embodiments, the organolithium compounds include lithiated alkylthioacetals such as 2-lithio-2-methyl-1,3-dithiane. These and related useful initiators are disclosed in U.S. Publ. Nos. 2006/0030657, 2006/0264590, and 2006/0264589, which are incorporated herein by reference. In still other embodiments, the organolithium compounds include alkoxysilyl-containing initiators, such as lithiated t-butyldimethylpropoxysilane. These and related useful initiators are disclosed in U.S. Publ. No. 2006/0241241, which is incorporated herein by reference.

In one or more embodiments, the anionic initiator employed is trialkyltinlithium compound such as tri-n-butyltinlithium. These and related useful initiators are disclosed in U.S. Pat. Nos. 3,426,006 and 5,268,439, which are incorporated herein by reference.

When elastomeric copolymers containing conjugated diene monomer and vinyl-substituted aromatic monomer are prepared by anionic polymerization, the conjugated diene monomer and vinyl-substituted aromatic monomer may be used at a weight ratio of 95:5 to 50:50, or in other embodiments, 90:10 to 65:35. In order to promote the randomization of comonomers in copolymerization and to control the microstructure (such as 1,2-linkage of conjugated diene monomer) of the polymer, a randomizer, which is typically a polar coordinator, may be employed along with the anionic initiator.

Compounds useful as randomizers include those having an oxygen or nitrogen heteroatom and a non-bonded pair of electrons. Exemplary types of randomizers include linear and cyclic oligomeric oxolanyl alkanes; dialkyl ethers of mono and oligo alkylene glycols (also known as glyme ethers); crown ethers; tertiary amines; linear THF oligomers; alkali metal alkoxides; and alkali metal sulfonates. Linear and cyclic oligomeric oxolanyl alkanes are described in U.S. Pat. No. 4,429,091, which is incorporated herein by reference. Specific examples of randomizers include 2,2-bis(2'-tetrahydrofuryl)propane, 1,2-dimethoxyethane, N,N,N',N'-tetramethylethylenediamine (TMEDA), tetrahydrofuran (THF), 1,2-dipiperidylethane, dipiperidylmethane, hexamethylphosphoramide, N,N'-dimethylpiperazine, diazabicyclooctane, dimethyl ether, diethyl ether, tri-n-butylamine, potassium t-amylate, potassium 4-dodecylsulfonate, and mixtures thereof.

The amount of randomizer to be employed may depend on various factors such as the desired microstructure of the polymer, the ratio of monomer to comonomer, the polymerization temperature, as well as the nature of the specific randomizer employed. In one or more embodiments, the amount of randomizer employed may range between 0.05 and 100 moles per mole of the anionic initiator.

The anionic initiator and the randomizer can be introduced to the polymerization system by various methods. In one or more embodiments, the anionic initiator and the randomizer may be added separately to the monomer to be polymerized in either a stepwise or simultaneous manner. In other embodiments, the anionic initiator and the randomizer may be pre-mixed outside the polymerization system either in the absence of any monomer or in the presence of a small amount of monomer, and the resulting mixture may be aged, if desired, and then added to the monomer that is to be polymerized.

In one or more embodiments, regardless of whether a coordination catalyst or an anionic initiator is used to prepare the reactive polymer, a solvent may be employed as a carrier to either dissolve or suspend the catalyst or initiator in order to facilitate the delivery of the catalyst or initiator to the polymerization system. In other embodiments, monomer can be used as the carrier. In yet other embodiments, the catalyst or initiator can be used in their neat state without any solvent.

In one or more embodiments, suitable solvents include those organic compounds that will not undergo polymerization or incorporation into propagating polymer chains during the polymerization of monomer in the presence of the catalyst or initiator. In one or more embodiments, these organic species are liquid at ambient temperature and pressure. In one or more embodiments, these organic solvents are inert to the catalyst or initiator. Exemplary organic solvents include hydrocarbons with a low or relatively low boiling point such as aromatic hydrocarbons, aliphatic hydrocarbons, and cycloaliphatic hydrocarbons. Non-limiting examples of aromatic hydrocarbons include benzene, toluene, xylenes, ethylbenzene, diethylbenzene, and mesitylene. Non-limiting examples of aliphatic hydrocarbons include n-pentane, n-hexane, n-heptane, n-octane, n-nonane, n-decane, isopentane, isohexanes, isopentanes, isooctanes, 2,2-dimethylbutane, petroleum ether, kerosene, and petroleum spirits. And, non-limiting examples of cycloaliphatic hydrocarbons include cyclopentane, cyclohexane, methylcyclopentane, and methylcyclohexane. Mixtures of the above hydrocarbons may also be used. As is known in the art, aliphatic and cycloaliphatic hydrocarbons may be desirably employed for environmental reasons. The low-boiling hydrocarbon solvents are typically separated from the polymer upon completion of the polymerization.

Other examples of organic solvents include high-boiling hydrocarbons of high molecular weights, including hydrocarbon oils that are commonly used to oil-extend polymers. Examples of these oils include paraffinic oils, aromatic oils, naphthenic oils, vegetable oils other than castor oils, and low PCA oils including MES, TDAE, SRAE, heavy naphthenic oils. Since these hydrocarbons are non-volatile, they typically do not require separation and remain incorporated in the polymer.

The production of the reactive polymer according to this invention can be accomplished by polymerizing conjugated diene monomer, optionally together with monomer copolymerizable with conjugated diene monomer, in the presence of a catalytically effective amount of the catalyst or initiator. The introduction of the catalyst or initiator, the conjugated diene monomer, optionally the comonomer, and any solvent, if employed, forms a polymerization mixture in which the reactive polymer is formed. The amount of the catalyst or initiator to be employed may depend on the interplay of various factors such as the type of catalyst or initiator employed, the purity of the ingredients, the polymerization temperature, the polymerization rate and conversion desired, the molecular weight desired, and many other factors. Accordingly, a specific catalyst or initiator amount cannot be definitively set forth except to say that catalytically effective amounts of the catalyst or initiator may be used.

In one or more embodiments, the amount of the coordinating metal compound (e.g., a lanthanide-containing compound) used can be varied from about 0.001 to about 2 mmol, in other embodiments from about 0.005 to about 1 mmol, and in still other embodiments from about 0.01 to about 0.2 mmol per 100 gram of monomer.

In other embodiments, where an anionic initiator (e.g., an alkyllithium compound) is employed, the initiator loading may be varied from about 0.05 to about 100 mmol, in other embodiments from about 0.1 to about 50 mmol, and in still other embodiments from about 0.2 to about 5 mmol per 100 gram of monomer.

In one or more embodiments, the polymerization may be carried out in a polymerization system that includes a substantial amount of solvent. In one embodiment, a solution polymerization system may be employed in which both the monomer to be polymerized and the polymer formed are soluble in the solvent. In another embodiment, a precipitation polymerization system may be employed by choosing a solvent in which the polymer formed is insoluble. In both cases, an amount of solvent in addition to the amount of solvent that may be used in preparing the catalyst or initiator is usually added to the polymerization system. The additional solvent may be the same as or different from the solvent used in preparing the catalyst or initiator. Exemplary solvents have been set forth above. In one or more embodiments, the solvent content of the polymerization mixture may be more than 20% by weight, in other embodiments more than 50% by weight, and in still other embodiments more than 80% by weight based on the total weight of the polymerization mixture.

In other embodiments, the polymerization system employed may be generally considered a bulk polymerization system that includes substantially no solvent or a minimal amount of solvent. Those skilled in the art will appreciate the benefits of bulk polymerization processes (i.e., processes where monomer acts as the solvent), and therefore the polymerization system includes less solvent than will deleteriously impact the benefits sought by conducting bulk polymerization. In one or more embodiments, the solvent content of the polymerization mixture may be less than about 20% by weight, in other embodiments less than about 10% by weight, and in still other embodiments less than about 5% by weight based on the total weight of the polymerization mixture. In another embodiment, the polymerization mixture contains no solvents other than those that are inherent to the raw materials employed. In still another embodiment, the polymerization mixture is substantially devoid of solvent, which refers to the absence of that amount of solvent that would otherwise have an appreciable impact on the polymerization process. Polymerization systems that are substantially devoid of solvent may be referred to as including substantially no solvent. In particular embodiments, the polymerization mixture is devoid of solvent.

The polymerization may be conducted in any conventional polymerization vessels known in the art. In one or more embodiments, solution polymerization can be conducted in a conventional stirred-tank reactor. In other embodiments, bulk polymerization can be conducted in a conventional stirred-tank reactor, especially if the monomer conversion is less than about 60%. In still other embodiments, especially where the monomer conversion in a bulk polymerization process is higher than about 60%, which typically results in a highly viscous cement, the bulk polymerization may be conducted in an elongated reactor in which the viscous cement under polymerization is driven to move by piston, or substantially by piston. For example, extruders in which the cement is pushed along by a self-cleaning single-screw or double-screw agitator are suitable for this purpose. Examples of useful bulk polymerization processes are disclosed in U.S. Pat. No. 7,351,776, which is incorporated herein by reference.

In one or more embodiments, all of the ingredients used for the polymerization can be combined within a single vessel (e.g., a conventional stirred-tank reactor), and all steps of the polymerization process can be conducted within this vessel. In other embodiments, two or more of the ingredients can be pre-combined in one vessel and then transferred to another vessel where the polymerization of monomer (or at least a major portion thereof) may be conducted.

The polymerization can be carried out as a batch process, a continuous process, or a semi-continuous process. In the semi-continuous process, the monomer is intermittently charged as needed to replace that monomer already polymerized. In one or more embodiments, the conditions under which the polymerization proceeds may be controlled to maintain the temperature of the polymerization mixture within a range from about −10° C. to about 200° C., in other embodiments from about 0° C. to about 150° C., and in other embodiments from about 20° C. to about 100° C. In one or more embodiments, the heat of polymerization may be removed by external cooling by a thermally controlled reactor jacket, internal cooling by evaporation and condensation of the monomer through the use of a reflux condenser connected to the reactor, or a combination of the two methods. Also, the polymerization conditions may be controlled to conduct the polymerization under a pressure of from about 0.1 atmosphere to about 50 atmospheres, in other embodiments from about 0.5 atmosphere to about 20 atmosphere, and in other embodiments from about 1 atmosphere to about 10 atmospheres. In one or more embodiments, the pressures at which the polymerization may be carried out include those that ensure that the majority of the monomer is in the liquid phase. In these or other embodiments, the polymerization mixture may be maintained under anaerobic conditions.

Regardless of whether the polymerization is catalyzed or initiated by a coordination catalyst (e.g., a lanthanide-based catalyst) or an anionic initiator (e.g., an alkyllithium initiator), some or all of the resulting polymer chains may possess reactive chain ends before the polymerization mixture is quenched. Thus, reference to a reactive polymer refers to a polymer having a reactive chain end deriving from a synthesis of the polymer by using a coordination catalyst or an anionic initiator. As noted above, the reactive polymer prepared with a coordination catalyst (e.g., a lanthanide-based catalyst) may be referred to as a pseudo-living polymer, and the reactive polymer prepared with an anionic initiator (e.g., an alkyllithium initiator) may be referred to as a living polymer. In one or more embodiments, a polymerization mixture including reactive polymer may be referred to as an active polymerization mixture. The percentage of polymer chains possessing a reactive end depends on various factors such as the type of catalyst or initiator, the type of monomer, the purity of the ingredients, the polymerization temperature, the monomer conversion, and many other factors. In one or more embodiments, at least about 20% of the polymer chains possess a reactive end, in other embodiments at least about 50% of the polymer chains possess a reactive end, and in still other embodiments at least about 80% of the polymer chains possess a reactive end. In any event, the reactive polymer can be reacted with a protected oxime compound containing a cyano group.

In one or more embodiments, protected oxime compounds containing a cyano group include those compounds that contain at least one protected oxime group and at least one cyano group. In one or more embodiments, the at least one oxime group may be directly tethered to the at least one cyano group via a bond. In other embodiments, the at least one oxime group may be indirectly tethered to the at least one cyano group via a divalent organic group.

As those skilled in the art appreciate, the cyano group, which can also be referred to as a nitrile group, may be defined by the formula —C≡N.

As those skilled in the art appreciate, an oxime group may be defined by the formula

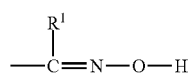

where $R^1$ is a hydrogen atom or a monovalent organic group. In one or more embodiments, a protected oxime group is an oxime group where the hydrogen atom bonded to the oxygen atom of the parent oxime group is replaced by a monovalent organic group. Accordingly, in one or more embodiments, a protected oxime group may be defined by the formula

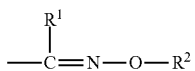

where $R^1$ is a hydrogen atom or a monovalent organic group and $R^2$ is a monovalent organic group.

In one or more embodiments, where $R^2$ is a hydrocarbyl group, the protected oxime group may be referred to as an O-hydrocarbyloxime group. In other embodiments, where $R^2$ is a silyl group, the protected oxime group may be referred to as an O-silyloxime group. In other embodiments, where $R^2$ is a sulfonyl group, the protected oxime group may be referred to as an O-sulfonyloxime group. In yet other embodiments, where $R^2$ is an acyl group, the protected oxime group may be referred to as an O-acyloxime group.

In one or more embodiments, a protected oxime compound containing a cyano group may be defined by the formula I:

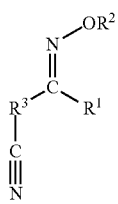

where $R^1$ is a hydrogen atom or monovalent organic group, $R^2$ is a monovalent organic group, and $R^3$ is a bond or a divalent organic group, or where $R^1$ and $R^3$ join to form a trivalent organic group. In one or more embodiments, where $R^1$ and $R^3$ of formula I join to form a trivalent organic group, the protected oxime compound containing a cyano group may be defined by the formula II:

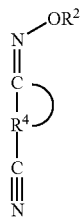

where $R^2$ is a monovalent organic group and $R^4$ is a trivalent organic group.

In one or more embodiments, the monovalent organic groups of the protected oxime compound containing a cyano group may be hydrocarbyl groups, which include, but are not limited to, alkyl, cycloalkyl, alkenyl, cycloalkenyl, aryl, allyl, aralkyl, alkaryl, or alkynyl groups. Hydrocarbyl groups also include substituted hydrocarbyl groups, which refer to hydrocarbyl groups in which one or more hydrogen atoms have been replaced by a substituent such as a hydrocarbyl, hydrocarbyloxy, silyl, or silyloxy group. In one or more embodiments, these groups may include from one, or the appropriate minimum number of carbon atoms to form the group, to about 20 carbon atoms. These groups may also contain heteroatoms such as, but not limited to, nitrogen, boron, oxygen, silicon, sulfur, tin, and phosphorus atoms.

In one or more embodiments, the monovalent organic groups of the protected oxime compound containing a cyano group may be silyl groups, which include, but are not limited to, trihydrocarbylsilyl, dihydrocarbylhydrosilyl, or hydrocarbyldihydrosilyl. Silyl groups also include substituted silyl groups, which refer to silyl groups in which one or more hydrogen atoms have been replaced by a substituent such as a hydrocarbyl, hydrocarbyloxy, silyl, or silyloxy group. In one or more embodiments, these groups may include from one, or the appropriate minimum number of carbon atoms to form the group, to about 20 carbon atoms. These groups may include heteroatoms such as, but not limited to, nitrogen, boron, oxygen, silicon, sulfur, tin, and phosphorus atoms, in addition to the parent silicon atom.

In one or more embodiments, the divalent organic groups of the protected oxime compound containing a cyano group may be hydrocarbylene groups, which include, but are not limited to, alkylene, cycloalkylene, alkenylene, cycloalkenylene, alkynylene, cycloalkynylene, or arylene groups. Hydrocarbylene groups include substituted hydrocarbylene groups, which refer to hydrocarbylene groups in which one or more hydrogen atoms have been replaced by a substituent such as a hydrocarbyl, hydrocarbyloxy, silyl, or silyloxy group. In one or more embodiments, these groups may include from one, or the appropriate minimum number of carbon atoms to form the group, to about 20 carbon atoms. These groups may also contain one or more heteroatoms such as, but not limited to, nitrogen, oxygen, boron, silicon, sulfur, tin, and phosphorus atoms.

In one or more embodiments, the monovalent, divalent, and/or trivalent groups of the protected oxime compound containing a cyano group may contain one or more oxime groups or cyano groups. For example, a cyano group may be pendently attached to $R^1$, $R^2$, or $R^3$ of formula I. In these embodiments, the protected oxime compound containing a cyano group may contain two or more cyano groups or oxime groups.

In one or more embodiments, where the protected oxime groups of the protected oxime compounds containing a cyano group are O-hydrocarbyloxime groups as described above, the protected oxime compounds containing a cyano group may be referred to as cyano O-hydrocarbyloximes. In other embodiments, where the protected oxime groups of the protected oxime compounds containing a cyano group are O-silyloxime groups as described above, the protected oxime compounds containing a cyano group may be referred to as cyano O-silyloximes. In other embodiments, where the protected oxime groups of the protected oxime compounds containing a cyano group are O-sulfonyloxime groups as described above, the protected oxime compounds containing a cyano group may be referred to as cyano O-sulfonyloximes. In yet other embodiments, where the protected oxime groups of the protected oxime compounds containing a cyano group are O-acyloxime groups as described above, the protected oxime compounds containing a cyano group may be referred to as cyano O-acyloximes.

Representative examples of cyano O-hydrocarbyloximes include cyanoformaldehyde O-methyloxime, 2-cyanoacetaldehyde O-methyloxime, 2-cyanopropionaldehyde O-methyloxime, 3-cyanobutyraldehyde O-methyloxime, 3-cyanopentanaldehyde O-methyloxime, 2-cyanocyclopentanecarboxaldehyde O-methyloxime, 6-cyanohexanaldehyde O-methyloxime, 3-cyanocyclohexanecarboxaldehyde O-methyloxime, 6-cyanoheptanaldehyde O-methyloxime, 4-cyanocycloheptanecarboxaldehyde O-methyloxime, 6-cyanooctanaldehyde O-methyloxime, 4-cyanocyclooctane carboxaldehyde O-methyloxime, 9-cyanononanaldehyde O-methyloxime, 3-cyanocyclononanecarboxaldehyde O-methyloxime, 2-cyanobenzaldehyde O-methyloxime, 3-cyanobenzaldehyde O-methyloxime, 4-cyanobenzaldehyde O-methyloxime, 4-cyano-trans-cinnamaldehyde O-methyloxime, 4-cyano-2-pyridinecarboxaldehyde O-methyloxime, 4-cyanotetrahydrofuran-3-carboxaldehyde O-methyloxime, 4-cyano-2-furancarboxaldehyde O-methyloxime, 2-cyano-3-furancarboxaldehyde O-methyloxime, 3-cyano-N-methyl-4-pyrazolecarboxaldehyde O-methyloxime, 4-cyano-N-methyl-2-pyrrolecarboxaldehyde O-methyloxime, 4-cyano-N-methyl-2-imidazolecarboxaldehyde O-methyloxime, 5-cyano-N-methyl-indole-3-carboxaldehyde O-methyloxime, 5-cyano-N-methyl-1,2,3-triazole-4-carboxaldehyde O-methyloxime, 5-cyano-N-methyl-1,2,4-triazole-3-carboxaldehyde O-methyloxime, 3-cyanopyrazinecarboxaldehyde O-methyloxime, 4-cyano-2-thiazolecarboxaldehyde O-methyloxime, 4-cyano-2-thiophenecarboxaldehyde O-methyloxime, cyanoformaldehyde O-benzyloxime, 2-cyanoacetaldehyde O-benzyloxime, 2-cyanopropionaldehyde O-benzyloxime, 3-cyanobutyraldehyde O-benzyloxime, 3-cyanopentanaldehyde O-benzyloxime, 2-cyanocyclopentanecarboxaldehyde O-benzyloxime, 6-cyanohexanaldehyde O-benzyloxime, 3-cyanocyclohexanecarboxaldehyde O-benzyloxime, 6-cyanoheptanaldehyde O-benzyloxime, 4-cyanocycloheptanecarboxaldehyde O-benzyloxime, 6-cyanooctanaldehyde O-benzyloxime, 4-cyanocyclooctanecarboxaldehyde O-benzyloxime, 9-cyanononanaldehyde O-benzyloxime, 3-cyanocyclononanecarboxaldehyde O-benzyloxime, 2-cyanobenzaldehyde O-benzyloxime, 3-cyanobenzaldehyde O-benzyloxime, 4-cyanobenzaldehyde O-benzyloxime, 4-cyano-trans-cinnamaldehyde O-benzyloxime, 4-cyano-2-pyridinecarboxaldehyde O-benzyloxime, 4-cyanotetrahydrofuran-3-carboxaldehyde O-benzyloxime, 4-cyano-2-furancarboxaldehyde O-benzyloxime, 2-cyano-3-furancarboxaldehyde O-benzyloxime, 3-cyano-N-methyl-4-pyrazolecarboxaldehyde O-benzyloxime, 4-cyano-N-methyl-2-pyrrolecarboxaldehyde O-benzyloxime, 4-cyano-N-methyl-2-imidazolecarboxaldehyde O-benzyloxime, 5-cyano-N-methyl-indole-3-carboxaldehyde O-benzyloxime, 5-cyano-N-methyl-1,2,3-triazole-4-carboxaldehyde O-benzyloxime, 5-cyano-N-methyl-1,2,4-triazole-3-carboxaldehyde O-benzyloxime, 3-cyanopyrazinecarboxaldehyde O-benzyloxime, 4-cyano-2-thiazolecarboxaldehyde O-benzyloxime, 4-cyano-2-thiophenecarboxaldehyde O-benzyloxime, 1-cyano-2-propanone O-methyloxime, 4-cyano-2-butanone O-methyloxime, 3-cyano-2-pentanone O-methyloxime, 1-cyano-3-pentanone O-methyloxime, 4-cyano-2-hexanone O-methyloxime, 1-cyano-3-hexanone O-methyloxime, 4-cyano-2-heptanone O-methyloxime, 1-cyano-3-heptanone O-methyloxime, 1-cyano-4-heptanone O-methyloxime, 5-cyano-2-octanone O-methyloxime, 5-cyano-3-octanone O-methyloxime, 9-cyano-2-nonanone O-methyloxime, 6-cyano-3-nonanone O-methyloxime, 1-cyano-5-nonanone O-methyloxime, 1-(2-cyanophenyl)ethan-1-one O-methyloxime, 1-(3-cyanophenyl)ethan-1-one O-methyloxime, 1-(4-cyanophenyl)ethan-1-one O-methyloxime, 1-(2-cyanocyclohexyl)ethan-1-one O-methyloxime, 1-(3-cyanocyclohexyl)ethan-1-one O-methyloxime, 1-(4-cyanocyclohexyl)ethan-1-one O-methyloxime, 2-cyanoacetophenone O-methyloxime, 3-cyanobenzophenone O-methyloxime, 4-cyanobenzophenone O-methyloxime, 2-cyanocyclobutanone O-methyloxime, 3-cyanocyclopentanone O-methyloxime, 2-cyanocyclohexanone O-methyloxime, 3-cyanocycloheptanone O-methyloxime, 4-cyanocyclooctanone O-methyloxime, 3-cyanocyclononanone O-methyloxime, 2-cyanocyclodecanone O-methyloxime, 4-cyanocycloundecanone O-methyloxime, 3-cyanocyclododecanone O-methyloxime, 4-cyanocyclotridecanone O-methyloxime, 4-cyano-1,3-dimethyl-2-imidazolidinone O-methyloxime, 1-(3-cyanothiophen-2-yl)ethan-1-one O-methyloxime, 1-(4-cyanothiazol-2-yl)ethan-1-one O-methyloxime, 1-(3-cyanopyridin-2-yl)ethan-1-one O-methyloxime, 1-(4-cyanopyridin-3-yl)ethan-1-one O-methyloxime, 1-(3-cyanopyridin-4-yl)ethan-1-one O-methyloxime, 4-cyano-bis(2-pyridyl)ketone O-methyloxime, 1-(3-cyano-1-methylpyrrolyl)ethan-1-one O-methyloxime, 1-(2-cyano-1-methylpyrrolyl)ethan-1-one O-methyloxime, 1-cyano-2-propanone O-benzyloxime, 4-cyano-2-butanone O-benzyloxime, 3-cyano-2-pentanone O-benzyloxime, 1-cyano-3-pentanone O-benzyloxime, 4-cyano-2-hexanone O-benzyloxime, 1-cyano-3-hexanone O-benzyloxime, 4-cyano-2-heptanone O-benzyloxime, 1-cyano-3-heptanone O-benzyloxime, 1-cyano-4-heptanone O-benzyloxime, 5-cyano-2-octanone O-benzyloxime, 5-cyano-3-octanone O-benzyloxime, 9-cyano-2-nonanone O-benzyloxime, 6-cyano-3-nonanone O-benzyloxime, 1-cyano-5-nonanone O-benzyloxime, 1-(2-cyanophenyl)ethan-1-one O-benzyloxime, 1-(3-cyanophenyl)ethan-1-one O-benzyloxime, 1-(4-cyanophenyl)ethan-1-one O-benzyloxime, 1-(2-cyanocyclohexyl)ethan-1-one O-benzyloxime, 1-(3-cyanocyclohexyl)ethan-1-one O-benzyloxime, 1-(4-cyanocyclohexyl)ethan-1-one O-benzyloxime, 2-cyanoacetophenone O-benzyloxime, 3-cyanobenzophenone O-benzyloxime, 4-cyanobenzophenone O-benzyloxime, 2-cyanocyclobutanone O-benzyloxime, 3-cyanocyclopentanone O-benzyloxime, 2-cyanocyclohexanone O-benzyloxime, 3-cyanocycloheptanone O-benzyloxime, 4-cyanocyclooctanone O-benzyloxime, 3-cyanocyclononanone O-benzyloxime, 2-cyanocyclodecanone O-benzyloxime, 4-cyanocycloundecanone O-benzyloxime, 3-cyanocyclododecanone O-benzyloxime, 4-cyanocyclotridecanone O-benzyloxime, 4-cyano-1,3-dimethyl-2-imidazolidinone O-benzyloxime, 1-(3-cyanothiophen-2-yl)ethan-1-one O-benzyloxime, 1-(4-cyanothiazol-2-yl)ethan-1-one O-benzyloxime, 1-(3-cyanopyridin-2-yl)ethan-1-one O-benzyloxime, 1-(4-cyanopyridin-3-yl)ethan-1-one O-benzyloxime, 1-(3-cyanopyridin-4-yl)ethan-1-one O-benzyloxime, 4-cyano-bis(2-pyridyl)ketone O-benzyloxime, 1-(3-cyano-1-methylpyrrolyl)ethan-1-one O-benzyloxime, and 1-(2-cyano-1-methylpyrrolyl)ethan-1-one O-benzyloxime.

Representative examples of cyano O-silyloximes include cyanoformaldehyde O-trimethylsilyloxime, 2-cyanoacetaldehyde O-trimethylsilyloxime, 2-cyanopropionaldehyde O-trimethylsilyloxime, 3-cyanobutyraldehyde O-trimethylsilyloxime, 3-cyanopentanaldehyde O-trimethylsilyloxime, 2-cyanocyclopentanecarboxaldehyde O-trimethylsilyloxime, 6-cyanohexanaldehyde O-trimethylsilyloxime, 3-cyanocyclohexanecarboxaldehyde O-trimethylsilyloxime, 6-cyanoheptanaldehyde O-trimethylsilyloxime, 4-cyanocycloheptanecarboxaldehyde O-trimethylsilyloxime, 6-cyanooctanaldehyde O-trimethylsilyloxime, 4-cyanocyclooctanecarboxaldehyde O-trimethylsilyloxime, 9-cyanononanaldehyde O-trimethylsilyloxime, 3-cyanoclononanecarboxaldehyde O-trimethylsilyloxime, 2-cyanobenzaldehyde O-trimethylsilyloxime, 3-cyanobenzaldehyde O-trimethylsilyloxime, 4-cyanobenzaldehyde O-trimethylsilyloxime, 4-cyano-trans-cinnamaldehyde O-trimethylsilyloxime, 4-cyano-2-pyridinecarboxaldehyde O-trimethylsilyloxime, 4-cyanotetrahydrofuran-3-carboxaldehyde O-trimethylsilyloxime, 4-cyano-2-furancarboxaldehyde O-trimethylsilyloxime, 2-cyano-3-furancarboxaldehyde O-trimethylsilyloxime, 3-cyano-N-methyl-4-pyrazolecarboxaldehyde O-trimethylsilyloxime, 4-cyano-N-methyl-2-pyrrolecarboxaldehyde O-trimethylsilyloxime, 4-cyano-N-methyl-2-imidazolecarboxaldehyde O-trimethylsilyloxime, 5-cyano-N-methyl-indole-3-carboxaldehyde O-trimethylsilyloxime, 5-cyano-N-methyl-1,2,3-triazole-4-carboxaldehyde O-trimethylsilyloxime, 5-cyano-N-methyl-1,2,4-triazole-3-carboxaldehyde O-trimethylsilyloxime, 3-cyanopyrazinecarboxaldehyde O-trimethylsilyloxime, 4-cyano-2-thiazolecarboxaldehyde O-trimethylsilyloxime, 4-cyano-2-thiophenecarboxaldehyde O-trimethylsilyloxime, cyanoformaldehyde O-triphenylsilyloxime, 2-cyanoacetaldehyde O-triphenylsilyloxime, 2-cyanopropionaldehyde O-triphenylsilyloxime, 3-cyanobutyraldehyde O-triphenylsilyloxime, 3-cyanopentanaldehyde O-triphenylsilyloxime, 2-cyanocyclopentanecarboxaldehyde O-triphenylsilyloxime, 6-cyanohexanaldehyde O-triphenylsilyloxime, 3-cyanocyclohexanecarboxaldehyde O-triphenylsilyloxime, 6-cyanoheptanaldehyde O-triphenylsilyloxime, 4-cyanocycloheptanecarboxaldehyde O-triphenylsilyloxime, 6-cyanooctanaldehyde O-triphenylsilyloxime, 4-cyanocyclooctanecarboxaldehyde O-triphenylsilyloxime, 9-cyanononanaldehyde O-triphenylsilyloxime, 3-cyanoclononanecarboxaldehyde O-triphenylsilyloxime, 2-cyanobenzaldehyde O-triphenylsilyloxime, 3-cyanobenzaldehyde O-triphenylsilyloxime, 4-cyanobenzaldehyde O-triphenylsilyloxime, 4-cyano-trans-cinnamaldehyde O-triphenylsilyloxime, 4-cyano-2-pyridinecarboxaldehyde O-triphenylsilyloxime, 4-cyanotetrahydrofuran-3-carboxaldehyde O-triphenylsilyloxime, 4-cyano-2-furancarboxaldehyde O-triphenylsilyloxime, 2-cyano-3-furancarboxaldehyde O-triphenylsilyloxime, 3-cyano-N-methyl-4-pyrazolecarboxaldehyde O-triphenylsilyloxime, 4-cyano-N-methyl-2-pyrrolecarboxaldehyde O-triphenylsilyloxime, 4-cyano-N-methyl-2-imidazolecarboxaldehyde O-triphenylsilyloxime, 5-cyano-N-methyl-indole-3-carboxaldehyde O-triphenylsilyloxime, 5-cyano-N-methyl-1,2,3-triazole-4-carboxaldehyde O-triphenylsilyloxime, 5-cyano-N-methyl-1,2,4-triazole-3-carboxaldehyde O-triphenylsilyloxime, 3-cyanopyrazinecarboxaldehyde O-triphenylsilyloxime, 4-cyano-2-thiazolecarboxaldehyde O-triphenylsilyloxime, 4-cyano-2-thiophenecarboxaldehyde O-triphenylsilyloxime, 1-cyano-2-propanone O-trimethylsilyloxime, 4-cyano-2-butanone O-trimethylsilyloxime, 3-cyano-2-pentanone O-trimethylsilyloxime, 1-cyano-3-pentanone O-trimethylsilyloxime, 4-cyano-2-hexanone O-trimethylsilyloxime, 1-cyano-3-hexanone O-trimethylsilyloxime, 4-cyano-2-heptanone O-trimethylsilyloxime, 1-cyano-3-heptanone O-trimethylsilyloxime, 1-cyano-4-heptanone O-trimethylsilyloxime, 5-cyano-2-octanone O-trimethylsilyloxime, 5-cyano-3-octanone O-trimethylsilyloxime, 9-cyano-2-nonanone O-trimethylsilyloxime, 6-cyano-3-nonanone O-trimethylsilyloxime, 1-cyano-5-nonanone O-trimethylsilyloxime, 1-(2-cyanophenyl)ethan-1-one O-trimethylsilyloxime, 1-(3-cyanophenyl)ethan-1-one O-trimethylsilyloxime, 1-(4-cyanophenyl)ethan-1-one O-trimethylsilyloxime, 1-(2-cyanocyclohexyl)ethan-1-one O-trimethylsilyloxime, 1-(3-cyanocyclohexyl)ethan-1-one O-trimethylsilyloxime, 1-(4-cyanocyclohexyl)ethan-1-one O-trimethylsilyloxime, 2-cyanoacetophenone O-trimethylsilyloxime, 3-cyanobenzophenone O-trimethylsilyloxime, 4-cyanobenzophenone O-trimethylsilyloxime, 2-cyanocyclobutanone O-trimethylsilyloxime, 3-cyanocyclopentanone O-trimethylsilyloxime, 2-cyanocyclohexanone O-trimethylsilyloxime, 3-cyanocycloheptanone O-trimethylsilyloxime, 4-cyanocyclooctanone O-trimethylsilyloxime, 3-cyanocyclononanone O-trimethylsilyloxime, 2-cyanocyclodecanone O-trimethylsilyloxime, 4-cyanocycloundecanone O-trimethylsilyloxime, 3-cyanocyclododecanone O-trimethylsilyloxime, 4-cyanocyclotridecanone O-trimethylsilyloxime, 4-cyano-1,3-dimethyl-2-imidazolidinone O-trimethylsilyloxime, 1-(3-cyanothiophen-2-yl)ethan-1-one O-trimethylsilyloxime, 1-(4-cyanothiazol-2-yl)ethan-1-one O-trimethylsilyloxime, 1-(3-cyanopyridin-2-yl)ethan-1-one O-trimethylsilyloxime, 1-(4-cyanopyridin-3-yl)ethan-1-one O-trimethylsilyloxime, 1-(3-cyanopyridin-4-yl)ethan-1-one O-trimethylsilyloxime, 4-cyano-bis(2-pyridyl)ketone O-trimethylsilyloxime, 1-(3-cyano-1-methylpyrrolyl)ethan-1-one O-trimethylsilyloxime, 1-(2-cyano-1-methylpyrrolyl)ethan-1-one O-trimethylsilyloxime, 1-cyano-2-propanone O-triphenylsilyloxime, 4-cyano-2-butanone O-triphenylsilyloxime, 3-cyano-2-pentanone O-triphenylsilyloxime, 1-cyano-3-pentanone O-triphenylsilyloxime, 4-cyano-2-hexanone O-triphenylsilyloxime, 1-cyano-3-hexanone O-triphenylsilyloxime, 4-cyano-2-heptanone O-triphenylsilyloxime, 1-cyano-3-heptanone O-triphenylsilyloxime, 1-cyano-4-heptanone O-triphenylsilyloxime, 5-cyano-2-octanone O-triphenylsilyloxime, 5-cyano-3-octanone O-triphenylsilyloxime, 9-cyano-2-nonanone O-triphenylsilyloxime, 6-cyano-3-nonanone O-triphenylsilyloxime, 1-cyano-5-nonanone O-triphenylsilyloxime, 1-(2-cyanophenyl)ethan-1-one O-triphenylsilyloxime, 1-(3-cyanophenyl)ethan-1-one O-triphenylsilyloxime, 1-(4-cyanophenyl)ethan-1-one O-triphenylsilyloxime, 1-(2-cyanocyclohexyl)ethan-1-one O-triphenylsilyloxime, 1-(3-cyanocyclohexyl)ethan-1-one O-triphenylsilyloxime, 1-(4-cyanocyclohexyl)ethan-1-one O-triphenylsilyloxime, 2-cyanoacetophenone O-triphenylsilyloxime, 3-cyanobenzophenone O-triphenylsilyloxime, 4-cyanobenzophenone O-triphenylsilyloxime, 2-cyanocyclobutanone O-triphenylsilyloxime, 3-cyanocyclopentanone O-triphenylsilyloxime, 2-cyanocyclohexanone O-triphenylsilyloxime, 3-cyanocycloheptanone O-triphenylsilyloxime, 4-cyanocyclooctanone O-triphenylsilyloxime, 3-cyanocyclononanone O-triphenylsilyloxime, 2-cyanocyclodecanone O-triphenylsilyloxime, 4-cyanocycloundecanone O-triphenylsilyloxime, 3-cyanocyclododecanone O-triphenylsilyloxime, 4-cyanocyclotridecanone O-triphenylsilyloxime, 4-cyano-1,3-dimethyl-2-imidazolidinone O-triphenylsilyloxime, 1-(3-cyanothiophen-2-yl)ethan-1-one O-triphenylsilyloxime, 1-(4-cyanothiazol-2-yl)ethan-1-one O-triphenylsilyloxime, 1-(3-cyanopyridin-2-yl)ethan-1-one O-triphenylsilyloxime, 1-(4-cyanopyridin-3-yl)ethan-1-one O-triphenylsilyloxime, 1-(3-cyanopyridin-4-yl)ethan-1-one O-triphenylsilyloxime, 4-cyano-bis(2-pyridyl)ketone O-triphenylsilyloxime, 1-(3-cyano-1-methylpyrrolyl)ethan-1-one O-triphenylsilyloxime, and 1-(2-cyano-1-methylpyrrolyl)ethan-1-one O-triphenylsilyloxime.

Representative examples of cyano O-sulfonyloximes include cyanoformaldehyde O-benzenesulfonyloxime, 2-cyanoacetaldehyde O-benzenesulfonyloxime, 2-cyanopropionaldehyde O-benzenesulfonyloxime, 3-cyanobutyraldehyde O-benzenesulfonyloxime, 3-cyanopentanaldehyde O-benzenesulfonyloxime, 2-cyanocyclopentanecarboxaldehyde O-benzenesulfonyloxime, 6-cyanohexanaldehyde O-benzenesulfonyloxime, 3-cyanocyclohexanecarboxaldehyde O-benzenesulfonyloxime, 6-cyanoheptanaldehyde O-benzenesulfonyloxime, 4-cyanocycloheptanecarboxaldehyde O-benzenesulfonyloxime, 6-cyanooctanaldehyde O-benzenesulfonyloxime, 4-cyanocyclooctanecarboxaldehyde O-benzenesulfonyloxime, 9-cyanononanaldehyde O-benzenesulfonyloxime, 3-cyanocyclononanecarboxaldehyde O-benzenesulfonyloxime, 2-cyanobenzaldehyde O-benzenesulfonyloxime, 3-cyanobenzaldehyde O-benzenesulfonyloxime, 4-cyanobenzaldehyde O-benzenesulfonyloxime, 4-cyano-trans-cinnamaldehyde O-benzenesulfonyloxime, 4-cyano-2-pyridinecarboxaldehyde O-benzenesulfonyloxime, 4-cyanotetrahydrofuran-3-carboxaldehyde O-benzenesulfonyloxime, 4-cyano-2-furancarboxaldehyde O-benzenesulfonyloxime, 2-cyano-3-furancarboxaldehyde O-benzenesulfonyloxime, 3-cyano-N-methyl-4-pyrazolecarboxaldehyde O-benzenesulfonyloxime, 4-cyano-N-methyl-2-pyrrolecarboxaldehyde O-benzenesulfonyloxime, 4-cyano-N-methyl-2-imidazolecarboxaldehyde O-benzenesulfonyloxime, 5-cyano-N-methyl-indole-3-carboxaldehyde O-benzenesulfonyloxime, 5-cyano-N-methyl-1,2,3-triazole-4-carboxaldehyde O-benzenesulfonyloxime, 5-cyano-N-methyl-1,2,4-triazole-3-carboxaldehyde O-benzenesulfonyloxime, 3-cyanopyrazinecarboxaldehyde O-benzenesulfonyloxime, 4-cyano-2-thiazolecarboxaldehyde O-benzenesulfonyloxime, 4-cyano-2-thiophenecarboxaldehyde O-benzenesulfonyloxime, 1-cyano-2-propanone O-benzenesulfonyloxime, 4-cyano-2-butanone O-benzenesulfonyloxime, 3-cyano-2-pentanone O-benzenesulfonyloxime, 1-cyano-3-pentanone O-benzenesulfonyloxime, 4-cyano-2-hexanone O-benzenesulfonyloxime, 1-cyano-3-hexanone O-benzenesulfonyloxime, 4-cyano-2-heptanone O-benzenesulfonyloxime, 1-cyano-3-heptanone O-benzenesulfonyloxime, 1-cyano-4-heptanone O-benzenesulfonyloxime, 5-cyano-2-octanone O-benzenesulfonyloxime, 5-cyano-3-octanone O-benzenesulfonyloxime, 9-cyano-2-nonanone O-benzenesulfonyloxime, 6-cyano-3-nonanone O-benzenesulfonyloxime, 1-cyano-5-nonanone O-benzenesulfonyloxime, 1-(2-cyanophenyl)ethan-1-one O-benzenesulfonyloxime, 1-(3-cyanophenyl)ethan-1-one O-benzenesulfonyloxime, 1-(4-cyanophenyl)ethan-1-one O-benzenesulfonyloxime, 1-(2-cyanocyclohexyl)ethan-1-one O-benzenesulfonyloxime, 1-(3-cyanocyclohexyl)ethan-1-one O-benzenesulfonyloxime, 1-(4-cyanocyclohexyl)ethan-1-one O-benzenesulfonyloxime, 2-cyanoacetophenone O-benzenesulfonyloxime, 3-cyanobenzophenone O-benzenesulfonyloxime, 4-cyanobenzophenone O-benzenesulfonyloxime, 2-cyanocyclobutanone O-benzenesulfonyloxime, 3-cyanocyclopentanone O-benzenesulfonyloxime, 2-cyanocyclohexanone O-benzenesulfonyloxime, 3-cyanocycloheptanone O-benzenesulfonyloxime, 4-cyanocyclooctanone O-benzenesulfonyloxime, 3-cyanocyclononanone O-benzenesulfonyloxime, 2-cyanocyclodecanone O-benzenesulfonyloxime, 4-cyanocycloundecanone O-benzenesulfonyloxime, 3-cyanocyclododecanone O-benzenesulfonyloxime, 4-cyanocyclotridecanone O-benzenesulfonyloxime, 4-cyano-1,3-dimethyl-2-imidazolidinone O-benzenesulfonyloxime, 1-(3-cyanothiophen-2-yl)ethan-1-one O-benzenesulfonyloxime, 1-(4-cyanothiazol-2-yl)ethan-1-one O-benzenesulfonyloxime, 1-(3-cyanopyridin-2-yl)ethan-1-one O-benzenesulfonyloxime, 1-(4-cyanopyridin-3-yl)ethan-1-one O-benzenesulfonyloxime, 1-(3-cyanopyridin-4-yl)ethan-1-one O-benzenesulfonyloxime, 4-cyano-bis(2-pyridyl)ketone O-benzenesulfonyloxime, 1-(3-cyano-1-methylpyrrolyl)ethan-1-one O-benzenesulfonyloxime, and 1-(2-cyano-1-methylpyrrolyl)ethan-1-one O-benzenesulfonyloxime.

Representative examples of cyano O-acyloximes include cyanoformaldehyde O-acetyloxime, 2-cyanoacetaldehyde O-acetyloxime, 2-cyanopropionaldehyde O-acetyloxime, 3-cyanobutyraldehyde O-acetyloxime, 3-cyanopentanaldehyde O-acetyloxime, 2-cyanocyclopentanecarboxaldehyde O-acetyloxime, 6-cyanohexanaldehyde O-acetyloxime, 3-cyanocyclohexanecarboxaldehyde O-acetyloxime, 6-cyanoheptanaldehyde O-acetyloxime, 4-cyanocycloheptanecarboxaldehyde O-acetyloxime, 6-cyanooctanaldehyde O-acetyloxime, 4-cyanocyclooctanecarboxaldehyde O-acetyloxime, 9-cyanononanaldehyde O-acetyloxime, 3-cyanocyclononanecarboxaldehyde O-acetyloxime, 2-cyanobenzaldehyde O-acetyloxime, 3-cyanobenzaldehyde O-acetyloxime, 4-cyanobenzaldehyde O-acetyloxime, 4-cyano-trans-cinnamaldehyde O-acetyloxime, 4-cyano-2-pyridinecarboxaldehyde O-acetyloxime, 4-cyanotetrahydrofuran-3-carboxaldehyde O-acetyloxime, 4-cyano-2-furancarboxaldehyde O-acetyloxime, 2-cyano-3-furancarboxaldehyde O-acetyloxime, 3-cyano-N-methyl-4-pyrazolecarboxaldehyde O-acetyloxime, 4-cyano-N-methyl-2-pyrrolecarboxaldehyde O-acetyloxime, 4-cyano-N-methyl-2-imidazolecarboxaldehyde O-acetyloxime, 5-cyano-N-methyl-indole-3-carboxaldehyde O-acetyloxime, 5-cyano-N-methyl-1,2,3-triazole-4-carboxaldehyde O-acetyloxime, 5-cyano-N-methyl-1,2,4-triazole-3-carboxaldehyde O-acetyloxime, 3-cyanopyrazinecarboxaldehyde O-acetyloxime, 4-cyano-2-thiazolecarboxaldehyde O-acetyloxime, 4-cyano-2-thiophenecarboxaldehyde O-acetyloxime, 1-cyano-2-propanone O-acetyloxime, 4-cyano-2-butanone O-acetyloxime, 3-cyano-2-pentanone O-acetyloxime, 1-cyano-3-pentanone O-acetyloxime, 4-cyano-2-hexanone O-acetyloxime, 1-cyano-3-hexanone O-acetyloxime, 4-cyano-2-heptanone O-acetyloxime, 1-cyano-3-heptanone O-acetyloxime, 1-cyano-4-heptanone O-acetyloxime, 5-cyano-2-octanone O-acetyloxime, 5-cyano-3-octanone O-acetyloxime, 9-cyano-2-nonanone O-acetyloxime, 6-cyano-3-nonanone O-acetyloxime, 1-cyano-5-nonanone O-acetyloxime, 1-(2-cyanophenyl)ethan-1-one O-acetyloxime, 1-(3-cyanophenyl)ethan-1-one O-acetyloxime, 1-(4-cyanophenyl)ethan-1-one O-acetyloxime, 1-(2-cyanocyclohexyl)ethan-1-one O-acetyloxime, 1-(3-cyanocyclohexyl)ethan-1-one O-acetyloxime, 1-(4-cyanocyclohexyl)ethan-1-one O-acetyloxime, 2-cyanoacetophenone O-acetyloxime, 3-cyanobenzophenone O-acetyloxime, 4-cyanobenzophenone O-acetyloxime, 2-cyanocyclobutanone O-acetyloxime, 3-cyanocyclopentanone O-acetyloxime, 2-cyanocyclohexanone O-acetyloxime, 3-cyanocycloheptanone O-acetyloxime, 4-cyanocyclooctanone O-acetyloxime, 3-cyanocyclononanone O-acetyloxime, 2-cyanocyclodecanone O-acetyloxime, 4-cyanocycloundecanone O-acetyloxime, 3-cyanocyclododecanone O-acetyloxime, 4-cyanocyclotridecanone O-acetyloxime, 4-cyano-1,3-dimethyl-2-imidazolidinone O-acetyloxime, 1-(3-cyanothiophen-2-yl)ethan-1-one O-acetyloxime, 1-(4-cyanothiazol-2-yl)ethan-1-one O-acetyloxime, 1-(3-cyanopyridin-2-yl)ethan-1-one O-acetyloxime, 1-(4-cyanopyridin-3-yl)ethan-1-one O-acetyloxime, 1-(3-cyanopyridin-4-yl)ethan-1-one O-acetyloxime, 4-cyano-bis(2-pyridyl) ketone O-acetyloxime, 1-(3-cyano-1-methylpyrrolyl)ethan-1-one O-acetyloxime, and 1-(2-cyano-1-methylpyrrolyl)ethan-1-one O-acetyloxime.

In one or more embodiments, the protected oxime compounds containing a cyano group may be prepared by reacting, via a condensation reaction, an aldehyde compound or a ketone compound containing a cyano group (i.e. N≡C—R—C(H)=O or N≡C—R—C(R)=O, respectively) with a protected hydroxylamine, which is a hydroxylamine in which the hydrogen atom of the hydroxyl group (—OH) of the parent hydroxylamine (i.e. $NH_2OH$) has been replaced by a monovalent organic group such as a hydrocarbyl or silyl group. The protected hydroxylamine may be generated in situ from a hydrochloride salt of the protected hydroxylamine, by reacting the hydrochloride salt of the protected hydroxylamine with a base to free the protected hydroxylamine. Amines are suitable bases for generating a protected hydroxylamine in situ. One mole of the aldehyde compound or ketone compound containing a cyano group can be reacted with one mole of protected hydroxylamine, or a slight excess of the protected hydroxylamine (e.g. about 1.2 moles), to form a condensation product, which is the protected oxime compound containing a cyano group. Alternatively, the protected oxime compounds containing a cyano group can be prepared by alkylating or silylating an unprotected oxime compounds containing a cyano group (i.e. the parent oxime compound containing a cyano group). The parent oxime compound containing a cyano group can be prepared by reacting, via a condensation reaction, an aldehyde compound or a ketone compound containing a cyano group with hydroxylamine.

The amount of the protected oxime compounds containing a cyano group that can be added to the polymerization mixture to yield the functionalized polymer of this invention may depend on various factors including the type and amount of catalyst or initiator used to synthesize the reactive polymer and the desired degree of functionalization. In one or more embodiments, where the reactive polymer is prepared by employing a lanthanide-based catalyst, the amount of the protected oxime compounds containing a cyano group employed can be described with reference to the lanthanide metal of the lanthanide-containing compound. For example, the molar ratio of the protected oxime compounds containing a cyano group to the lanthanide metal may be from about 1:1 to about 200:1, in other embodiments from about 5:1 to about 150:1, and in other embodiments from about 10:1 to about 100:1.

In other embodiments, such as where the reactive polymer is prepared by using an anionic initiator, the amount of the protected oxime compounds containing a cyano group employed can be described with reference to the amount of metal cation associated with the initiator. For example, where an organolithium initiator is employed, the molar ratio of the protected oxime compounds containing a cyano group to the lithium cation may be from about 0.3:1 to about 2:1, in other embodiments from about 0.6:1 to about 1.5:1, and in other embodiments from 0.8:1 to about 1.2:1.

In one or more embodiments, in addition to the protected oxime compound containing a cyano group, a co-functionalizing agent may also be added to the polymerization mixture to yield a functionalized polymer with tailored properties. A mixture of two or more co-functionalizing agents may also be employed. The co-functionalizing agent may be added to the polymerization mixture prior to, together with, or after the introduction of the protected oxime compound containing a cyano group. In one or more embodiments, the co-functionalizing agent is added to the polymerization mixture at least 5 minutes after, in other embodiments at least 10 minutes after, and in other embodiments at least 30 minutes after the introduction of the protected oxime compound containing a cyano group.

In one or more embodiments, co-functionalizing agents include compounds or reagents that can react with a reactive polymer produced by this invention and thereby provide the polymer with a functional group that is distinct from a propagating chain that has not been reacted with the co-functionalizing agent. The functional group may be reactive or interactive with other polymer chains (propagating and/or non-propagating) or with other constituents such as reinforcing fillers (e.g. carbon black) that may be combined with the polymer. In one or more embodiments, the reaction between the co-functionalizing agent and the reactive polymer proceeds via an addition or substitution reaction.

Useful co-functionalizing agents may include compounds that simply provide a functional group at the end of a polymer chain without joining two or more polymer chains together, as well as compounds that can couple or join two or more polymer chains together via a functional linkage to form a single macromolecule. The latter type of co-functionalizing agents may also be referred to as coupling agents.

In one or more embodiments, co-functionalizing agents include compounds that will add or impart a heteroatom to the polymer chain. In particular embodiments, co-functionalizing agents include those compounds that will impart a functional group to the polymer chain to form a functionalized polymer that reduces the 50° C. hysteresis loss of a carbon-black filled vulcanizates prepared from the functionalized polymer as compared to similar carbon-black filled vulcanizates prepared from non-functionalized polymer. In one or more embodiments, this reduction in hysteresis loss is at least 5%, in other embodiments at least 10%, and in other embodiments at least 15%.

In one or more embodiments, suitable co-functionalizing agents include those compounds that contain groups that may react with the reactive polymers produced in accordance with this invention. Exemplary co-functionalizing agents include ketones, quinones, aldehydes, amides, esters, isocyanates, isothiocyanates, epoxides, imines, aminoketones, aminothioketones, and acid anhydrides. Examples of these compounds are disclosed in U.S. Pat. Nos. 4,906,706, 4,990,573, 5,064,910, 5,567,784, 5,844,050, 6,838,526, 6,977,281, and 6,992,147; U.S. Pat. Publication Nos. 2006/0004131 A1, 2006/0025539 A1, 2006/0030677 A1, and 2004/0147694 A1; Japanese Patent Application Nos. 05-051406A, 05-059103A, 10-306113A, and 11-035633A; which are incorporated herein by reference. Other examples of co-functionalizing agents include azine compounds as described in U.S. Pat. No. 7,879,952, hydrobenzamide compounds as disclosed in U.S. Pat. No. 7,671,138, nitro compounds as disclosed in U.S. Pat. No. 7,732,534, and protected oxime compounds as disclosed in U.S. Pat. No. 8,088,868, all of which are incorporated herein by reference.

In particular embodiments, the co-functionalizing agents employed may be metal halides, metalloid halides, alkoxysilanes, metal carboxylates, hydrocarbylmetal carboxylates, hydrocarbylmetal ester-carboxylates, and metal alkoxides.

Exemplary metal halide compounds include tin tetrachloride, tin tetrabromide, tin tetraiodide, n-butyltin trichloride, phenyltin trichloride, di-n-butyltin dichloride, diphenyltin dichloride, tri-n-butyltin chloride, triphenyltin chloride, germanium tetrachloride, germanium tetrabromide, germanium tetraiodide, n-butylgermanium trichloride, di-n-butylgermanium dichloride, and tri-n-butylgermanium chloride.

Exemplary metalloid halide compounds include silicon tetrachloride, silicon tetrabromide, silicon tetraiodide, methyltrichlorosilane, phenyltrichlorosilane, dimethyldichlorosilane, diphenyldichlorosilane, boron trichloride, boron tribromide, boron triiodide, phosphorous trichloride, phosphorous tribromide, and phosphorus triiodide.

In one or more embodiments, the alkoxysilanes may include at least one group selected from the group consisting of an epoxy group and an isocyanate group.

Exemplary alkoxysilane compounds including an epoxy group include (3-glycidyloxypropyl)trimethoxysilane, (3-glycidyloxypropyl)triethoxysilane, (3-glycidyloxypropyl)triphenoxysilane, (3-glycidyloxypropyl)methyldimethoxysilane, (3-glycidyloxypropyl)methyldiethoxysilane, (3-glycidyloxypropyl)methyldiphenoxysilane, [2-(3,4-epoxycyclohexyl)ethyl]trimethoxysilane, and [2-(3,4-epoxycyclohexyl)ethyl]triethoxysilane.

Exemplary alkoxysilane compounds including an isocyanate group include (3-isocyanatopropyl)trimethoxysilane, (3-isocyanatopropyl)triethoxysilane, (3-isocyanatopropyl)triphenoxysilane, (3-isocyanatopropyl)methyldimethoxysilane, (3-isocyanatopropyl)methyldiethoxysilane (3-isocyanatopropyl)methyldiphenoxysilane, and (isocyanatomethyl)methyldimethoxysilane.

Exemplary metal carboxylate compounds include tin tetraacetate, tin bis(2-ethylhexanaote), and tin bis(neodecanoate).

Exemplary hydrocarbylmetal carboxylate compounds include triphenyltin 2-ethylhexanoate, tri-n-butyltin 2-ethylhexanoate, tri-n-butyltin neodecanoate, triisobutyltin 2-ethylhexanoate, diphenyltin bis(2-ethylhexanoate), di-n-butyltin bis(2-ethylhexanoate), di-n-butyltin bis(neodecanoate), phenyltin tris(2-ethylhexanoate), and n-butyltin tris(2-ethylhexanoate).

Exemplary hydrocarbylmetal ester-carboxylate compounds include di-n-butyltin bis(n-octylmaleate), di-n-octyltin bis(n-octylmaleate), diphenyltin bis(n-octylmaleate), di-n-butyltin bis(2-ethylhexylmaleate), di-n-octyltin bis(2-ethylhexylmaleate), and diphenyltin bis(2-ethylhexylmaleate).

Exemplary metal alkoxide compounds include dimethoxytin, diethoxytin, tetraethoxytin, tetra-n-propoxytin, tetraisopropoxytin, tetra-n-butoxytin, tetraisobutoxytin, tetra-t-butoxytin, and tetraphenoxytin.

The amount of the co-functionalizing agent that can be added to the polymerization mixture may depend on various factors including the type and amount of catalyst or initiator used to synthesize the reactive polymer and the desired degree of functionalization. In one or more embodiments, where the reactive polymer is prepared by employing a lanthanide-based catalyst, the amount of the co-functionalizing agent employed can be described with reference to the lanthanide metal of the lanthanide-containing compound. For example, the molar ratio of the co-functionalizing agent to the lanthanide metal may be from about 1:1 to about 200:1, in other embodiments from about 5:1 to about 150:1, and in other embodiments from about 10:1 to about 100:1.

In other embodiments, such as where the reactive polymer is prepared by using an anionic initiator, the amount of the co-functionalizing agent employed can be described with reference to the amount of metal cation associated with the initiator. For example, where an organolithium initiator is employed, the molar ratio of the co-functionalizing agent to the lithium cation may be from about 0.3:1 to about 2:1, in other embodiments from about 0.6:1 to about 1.5:1, and in other embodiments from 0.8:1 to about 1.2:1.

The amount of the co-functionalizing agent employed can also be described with reference to the protected oxime compound containing a cyano group. In one or more embodiments, the molar ratio of the co-functionalizing agent to the protected oxime compound containing a cyano group may be from about 0.05:1 to about 1:1, in other embodiments from about 0.1:1 to about 0.8:1, and in other embodiments from about 0.2:1 to about 0.6:1.

In one or more embodiments, the protected oxime compound containing a cyano group (and optionally the co-functionalizing agent) may be introduced to the polymerization mixture at a location (e.g., within a vessel) where the polymerization has been conducted. In other embodiments, the protected oxime compound containing a cyano group may be introduced to the polymerization mixture at a location that is distinct from where the polymerization has taken place. For example, the protected oxime compound containing a cyano group may be introduced to the polymerization mixture in downstream vessels including downstream reactors or tanks, in-line reactors or mixers, extruders, or devolatilizers.

In one or more embodiments, the protected oxime compound containing a cyano group (and optionally the co-functionalizing agent) can be reacted with the reactive polymer after a desired monomer conversion is achieved but before the polymerization mixture is quenched by a quenching agent. In one or more embodiments, the reaction between the protected oxime compound containing a cyano group and the reactive polymer may take place within 30 minutes, in other embodiments within 5 minutes, and in other embodiments within one minute after the peak polymerization temperature is reached. In one or more embodiments, the reaction between the protected oxime compound containing a cyano group and the reactive polymer can occur once the peak polymerization temperature is reached. In other embodiments, the reaction between the protected oxime compound containing a cyano group and the reactive polymer can occur after the reactive polymer has been stored. In one or more embodiments, the storage of the reactive polymer occurs at room temperature or below room temperature under an inert atmosphere. In one or more embodiments, the reaction between the protected oxime compound containing a cyano group and the reactive polymer may take place at a temperature from about 10° C. to about 150° C., and in other embodiments from about 20° C. to about 100° C. The time required for completing the reaction between the protected oxime compound containing a cyano group and the reactive polymer depends on various factors such as the type and amount of the catalyst or initiator used to prepare the reactive polymer, the type and amount of the protected oxime compound containing a cyano group, as well as the temperature at which the functionalization reaction is conducted. In one or more embodiments, the reaction between the protected oxime compound containing a cyano group and the reactive polymer can be conducted for about 10 to 60 minutes.

In one or more embodiments, after the reaction between the reactive polymer and the protected oxime compound containing a cyano group (and optionally the co-functionalizing agent) has been accomplished or completed, a quenching agent can be added to the polymerization mixture in order to protonate the reaction product between the reactive polymer and the protected oxime compound containing a cyano group, inactivate any residual reactive polymer chains, and/or inactivate the catalyst or catalyst components. The quenching agent may include a protic compound, which includes, but is not limited to, an alcohol, a carboxylic acid, an inorganic acid, water, or a mixture thereof. An antioxidant such as 2,6-di-tert-butyl-4-methylphenol may be added along with, before, or after the addition of the quenching agent. The amount of the antioxidant employed may be in the range of 0.2% to 1% by weight of the polymer product. Additionally, the polymer product can be oil extended by adding an oil to the polymer, which may be in the form of a polymer cement or polymer dissolved or suspended in monomer. Practice of the present invention does not limit the amount of oil that may be added, and therefore conventional amounts may be added (e.g., 5-50 phr). Useful oils or extenders that may be employed include, but are not limited to, aromatic oils, paraffinic oils, naphthenic oils, vegetable oils other than castor oils, low PCA oils including MES, TDAE, and SRAE, and heavy naphthenic oils.

Once the polymerization mixture has been quenched, the various constituents of the polymerization mixture may be recovered. In one or more embodiments, the unreacted monomer can be recovered from the polymerization mixture. For example, the monomer can be distilled from the polymerization mixture by using techniques known in the art. In one or more embodiments, a devolatilizer may be employed to remove the monomer from the polymerization mixture. Once the monomer has been removed from the polymerization mixture, the monomer may be purified, stored, and/or recycled back to the polymerization process.

The polymer product may be recovered from the polymerization mixture by using techniques known in the art. In one or more embodiments, desolventization and drying techniques may be used. For instance, the polymer can be recovered by passing the polymerization mixture through a heated screw apparatus, such as a desolventizing extruder, in which the volatile substances are removed by evaporation at appropriate temperatures (e.g., about 100° C. to about 170° C.) and under atmospheric or sub-atmospheric pressure. This treatment serves to remove unreacted monomer as well as any low-boiling solvent. Alternatively, the polymer can also be recovered by subjecting the polymerization mixture to steam desolventization, followed by drying the resulting polymer crumbs in a hot air tunnel. The polymer can also be recovered by directly drying the polymerization mixture on a drum dryer.

The reactive polymer and the protected oxime compound containing a cyano group (and optionally the co-functionalizing agent) are believed to react to produce a novel functionalized polymer, wherein the residue of the protected oxime compound containing a cyano group is imparted to the end of the polymer chain. It is believed that the reactive end of the polymer chain reacts with the protected oxime compound containing a cyano group. Nonetheless, the exact chemical structure of the functionalized polymer produced in every embodiment is not known with any great degree of certainty, particularly as the structure relates to the residue imparted to the polymer chain end by the protected oxime compound containing a cyano group and optionally the co-functionalizing agent. Indeed, it is speculated that the structure of the functionalized polymer may depend upon various factors such as the conditions employed to prepare the reactive polymer (e.g., the type and amount of the catalyst or initiator) and the conditions employed to react the protected oxime compound containing a cyano group (and optionally the co-functionalizing agent) with the reactive polymer (e.g., the types and amounts of the protected oxime compound containing a cyano group and the co-functionalizing agent). The functionalized polymer resulting from the reaction between the reactive polymer and protected oxime compound containing a cyano group can be protonated or further modified.

In one or more embodiments, the functionalized polymers prepared according to this invention may contain unsaturation. In these or other embodiments, the functionalized polymers are vulcanizable. In one or more embodiments, the functionalized polymers can have a glass transition temperature ($T_g$) that is less than 0° C., in other embodiments less than −20° C., and in other embodiments less than −30° C. In one embodiment, these polymers may exhibit a single glass transition temperature. In particular embodiments, the polymers may be hydrogenated or partially hydrogenated.

In one or more embodiments, the functionalized polymers of this invention may be cis-1,4-polydienes having a cis-1,4-linkage content that is greater than 60%, in other embodiments greater than about 75%, in other embodiments greater than about 90%, and in other embodiments greater than about 95%, where the percentages are based upon the number of diene mer units adopting the cis-1,4 linkage versus the total number of diene mer units. Also, these polymers may have a 1,2-linkage content that is less than about 7%, in other embodiments less than 5%, in other embodiments less than 2%, and in other embodiments less than 1%, where the percentages are based upon the number of diene mer units adopting the 1,2-linkage versus the total number of diene mer units. The balance of the diene mer units may adopt the trans-1,4-linkage. The cis-1,4-, 1,2-, and trans-1,4-linkage contents can be determined by infrared spectroscopy. The number average molecular weight ($M_n$) of these polymers may be from about 1,000 to about 1,000,000, in other embodiments from about 5,000 to about 200,000, in other embodiments from about 25,000 to about 150,000, and in other embodiments from about 50,000 to about 120,000, as determined by using gel permeation chromatography (GPC) calibrated with polystyrene standards and Mark-Houwink constants for the polymer in question. The molecular weight distribution or polydispersity ($M_w/M_n$) of these polymers may be from about 1.5 to about 5.0, and in other embodiments from about 2.0 to about 4.0.

In one or more embodiments, the functionalized polymers of this invention may be polydienes having medium or low cis-1,4-linkage contents. These polymers, which can be prepared by anionic polymerization techniques, can have a cis-1,4-linkage content of from about 10% to 60%, in other embodiments from about 15% to 55%, and in other embodiments from about 20% to about 50%. These polydienes may also have a 1,2-linkage content from about 10% to about 90%, in other embodiments from about 10% to about 60%, in other embodiments from about 15% to about 50%, and in other embodiments from about 20% to about 45%. In particular embodiments, where the polydienes are prepared by employing a functional anionic initiator, the head of the polymer chain includes a functional group that is the residue of the functional initiator.

In particular embodiments, the functionalized polymers of this invention are copolymers of 1,3-butadiene, styrene, and optionally isoprene. These may include random copolymers and block copolymers.

Advantageously, the functionalized polymers of this invention may provide rubber compositions that demonstrate reduced hysteresis. The functionalized polymers are particularly useful in preparing rubber compositions that can be used to manufacture tire components. Rubber compounding techniques and the additives employed therein are generally disclosed in *The Compounding and Vulcanization of Rubber, in Rubber Technology* ($2^{nd}$ Ed. 1973).

The rubber compositions can be prepared by using the functionalized polymers alone or together with other elastomers (i.e., polymers that can be vulcanized to form compositions possessing rubbery or elastomeric properties). Other elastomers that may be used include natural and synthetic rubbers. The synthetic rubbers typically derive from the polymerization of conjugated diene monomer, the copolymerization of conjugated diene monomer with other monomer such as vinyl-substituted aromatic monomer, or the copolymerization of ethylene with one or more α-olefins and optionally one or more diene monomers.

Exemplary elastomers include natural rubber, synthetic polyisoprene, polybutadiene, polyisobutylene-co-isoprene, neoprene, poly(ethylene-co-propylene), poly(styrene-co-butadiene), poly(styrene-co-isoprene), poly(styrene-co-isoprene-co-butadiene), poly(isoprene-co-butadiene), poly(ethylene-co-propylene-co-diene), polysulfide rubber, acrylic rubber, urethane rubber, silicone rubber, epichlorohydrin rubber, and mixtures thereof. These elastomers can have a myriad of macromolecular structures including linear, branched, and star-shaped structures.

The rubber compositions may include fillers such as inorganic and organic fillers. Examples of organic fillers include carbon black and starch. Examples of inorganic fillers include silica, aluminum hydroxide, magnesium hydroxide, mica, talc (hydrated magnesium silicate), and clays (hydrated aluminum silicates). Carbon blacks and silicas are the most common fillers used in manufacturing tires. In certain embodiments, a mixture of different fillers may be advantageously employed.

In one or more embodiments, carbon blacks include furnace blacks, channel blacks, and lamp blacks. More specific examples of carbon blacks include super abrasion furnace blacks, intermediate super abrasion furnace blacks, high abrasion furnace blacks, fast extrusion furnace blacks, fine furnace blacks, semi-reinforcing furnace blacks, medium processing channel blacks, hard processing channel blacks, conducting channel blacks, and acetylene blacks.

In particular embodiments, the carbon blacks may have a surface area (EMSA) of at least 20 $m^2/g$ and in other embodiments at least 35 $m^2/g$; surface area values can be determined by ASTM D-1765 using the cetyltrimethylammonium bromide (CTAB) technique. The carbon blacks may be in a pelletized form or an unpelletized flocculent form. The preferred form of carbon black may depend upon the type of mixing equipment used to mix the rubber compound.

The amount of carbon black employed in the rubber compositions can be up to about 50 parts by weight per 100 parts by weight of rubber (phr), with about 5 to about 40 phr being typical.

Some commercially available silicas which may be used include Hi-Sil™ 215, Hi-Sil™ 233, and Hi-Sil™ 190 (PPG Industries, Inc.; Pittsburgh, Pa.). Other suppliers of commercially available silica include Grace Davison (Baltimore, Md.), Degussa Corp. (Parsippany, N.J.), Rhodia Silica Systems (Cranbury, N.J.), and J.M. Huber Corp. (Edison, N.J.).

In one or more embodiments, silicas may be characterized by their surface areas, which give a measure of their reinforcing character. The Brunauer, Emmet and Teller ("BET") method (described in *J. Am. Chem. Soc., vol.* 60, p. 309 et seq.) is a recognized method for determining the surface area. The BET surface area of silica is generally less than 450 $m^2/g$. Useful ranges of surface area include from about 32 to about 400 $m^2/g$, about 100 to about 250 $m^2/g$, and about 150 to about 220 $m^2/g$.

The pH's of the silicas are generally from about 5 to about 7 or slightly over 7, or in other embodiments from about 5.5 to about 6.8.

In one or more embodiments, where silica is employed as a filler (alone or in combination with other fillers), a coupling agent and/or a shielding agent may be added to the rubber compositions during mixing in order to enhance the interaction of silica with the elastomers. Useful coupling agents and shielding agents are disclosed in U.S. Pat. Nos. 3,842,111, 3,873,489, 3,978,103, 3,997,581, 4,002,594, 5,580,919, 5,583,245, 5,663,396, 5,674,932, 5,684,171, 5,684,172 5,696,197, 6,608,145, 6,667,362, 6,579,949, 6,590,017, 6,525,118, 6,342,552, and 6,683,135, which are incorporated herein by reference.

The amount of silica employed in the rubber compositions can be from about 1 to about 100 phr or in other embodiments from about 5 to about 80 phr. The useful upper range is limited by the high viscosity imparted by silicas. When silica is used together with carbon black, the amount of silica can be decreased to as low as about 1 phr; as the amount of silica is decreased, lesser amounts of coupling agents and shielding agents can be employed. Generally, the amounts of coupling agents and shielding agents range from about 4% to about 20% based on the weight of silica used.

A multitude of rubber curing agents (also called vulcanizing agents) may be employed, including sulfur or peroxide-based curing systems. Curing agents are described in *Kirk-Othmer, ENCYCLOPEDIA OF CHEMICAL TECHNOLOGY*, Vol. 20, pgs. 365-468, ($3^{rd}$ Ed. 1982), particularly *Vulcanization Agents and Auxiliary Materials*, pgs. 390-402, and A. Y. Coran, *Vulcanization, ENCYCLOPEDIA OF POLYMER SCIENCE AND ENGINEERING*, ($2^{nd}$ Ed. 1989), which are incorporated herein by reference. Vulcanizing agents may be used alone or in combination.

Other ingredients that are typically employed in rubber compounding may also be added to the rubber compositions. These include accelerators, accelerator activators, oils, plasticizer, waxes, scorch inhibiting agents, processing aids, zinc oxide, tackifying resins, reinforcing resins, fatty acids such as stearic acid, peptizers, and antidegradants such as antioxidants and antiozonants. In particular embodiments, the oils that are employed include those conventionally used as extender oils, which are described above.

All ingredients of the rubber compositions can be mixed with standard mixing equipment such as Banbury or Brabender mixers, extruders, kneaders, and two-rolled mills. In one or more embodiments, the ingredients are mixed in two or more stages. In the first stage (often referred to as the masterbatch mixing stage), a so-called masterbatch, which typically includes the rubber component and filler, is prepared. To prevent premature vulcanization (also known as scorch), the masterbatch may exclude vulcanizing agents. The masterbatch may be mixed at a starting temperature of from about 25° C. to about 125° C. with a discharge temperature of about 135° C. to about 180° C. Once the masterbatch is prepared, the vulcanizing agents may be introduced and mixed into the masterbatch in a final mixing stage, which is typically conducted at relatively low temperatures so as to reduce the chances of premature vulcanization. Optionally, additional mixing stages, sometimes called remills, can be employed between the masterbatch mixing stage and the final mixing stage. One or more remill stages are often employed where the rubber composition includes silica as the filler. Various ingredients including the functionalized polymers of this invention can be added during these remills.

The mixing procedures and conditions particularly applicable to silica-filled tire formulations are described in U.S. Pat. Nos. 5,227,425, 5,719,207, and 5,717,022, as well as European Patent No. 890,606, all of which are incorporated herein by reference. In one embodiment, the initial masterbatch is prepared by including the functionalized polymer of this invention and silica in the substantial absence of coupling agents and shielding agents.

The rubber compositions prepared from the functionalized polymers of this invention are particularly useful for forming tire components such as treads, subtreads, sidewalls, body ply skims, bead filler, and the like. Preferably, the functional polymers of this invention are employed in tread and sidewall formulations. In one or more embodiments, these tread or sidewall formulations may include from about 10% to about 100% by weight, in other embodiments from about 35% to about 90% by weight, and in other embodiments from about 50% to about 80% by weight of the functionalized polymer based on the total weight of the rubber within the formulation.

Where the rubber compositions are employed in the manufacture of tires, these compositions can be processed into tire components according to ordinary tire manufacturing techniques including standard rubber shaping, molding and curing techniques. Typically, vulcanization is effected by heating the vulcanizable composition in a mold; e.g., it may be heated to about 140° C. to about 180° C. Cured or crosslinked rubber compositions may be referred to as vulcanizates, which generally contain three-dimensional polymeric networks that are thermoset. The other ingredients, such as fillers and processing aids, may be evenly dispersed throughout the crosslinked network. Pneumatic tires can be made as discussed in U.S. Pat. Nos. 5,866,171, 5,876,527, 5,931,211, and 5,971,046, which are incorporated herein by reference.

In order to demonstrate the practice of the present invention, the following examples have been prepared and tested. The examples should not, however, be viewed as limiting the scope of the invention. The claims will serve to define the invention.

EXAMPLES

Example 1

Synthesis of 2-Cyanobenzaldehyde O-Methyloxime (Cyano-Oxime A)

Methoxylamine hydrochloride (1.83 g, 21.96 mmol) was added to a mixture of 2-cyanobenzaldehyde (2.40 g, 18.30 mmol) in $CH_2Cl_2$ (55 ml) at room temperature. Pyridine (5.92 ml, 73.21 mmol) was then added and the resulting mixture was stirred for 5 hours at room temperature. The mixture was concentrated under vacuum and the resulting solid was run through a short plug of silica with $CH_2Cl_2$ to afford 2-cyanobenzaldehyde O-methyloxime (abbreviated as cyano-oxime A) as a white solid (2.80 g, 95.5% yield). The $^1H$ NMR data ($CDCl_3$, 25° C., referenced to tetramethylsilane) of the product is listed as follows: δ 8.43 (s, 1H), 7.98 (dd, 1H), 7.67 (dd, 1H), 7.59 (dt, 1H), 7.45 (dt, 1H), 4.04 (s, 3H). From the $^1H$ NMR data, the structure of the product was determined to be as follows:

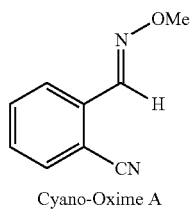 [SMILES: CO/N=C/c1ccccc1C#N]

Cyano-Oxime A

Example 2

Synthesis of 4-Cyanobenzaldehyde O-Methyloxime (Cyano-Oxime B)

Sodium hydroxide (0.79 g, 19.67 mmol) was added to a mixture of methoxylamine hydrochloride (1.64 g, 19.67 mmol) in $H_2O$ (70 ml) at room temperature. 4-Cyanobenzaldehyde (2.15 g, 16.40 mmol) was then added, and the resulting mixture was stirred for 1 hour at room temperature. The mixture was then extracted twice with ethyl acetate (EtOAc) and the organic layers were combined, dried over $Na_2SO_4$, and concentrated under vacuum. The resulting solid was then recrystallized in a 1:1 mixture of MeOH: Hexanes to afford 4-cyanobenzaldehyde O-methyloxime (abbreviated as cyano-oxime B) as a white crystalline solid (1.70 g, 65% yield). The $^1H$ NMR data ($CDCl_3$, 25° C., referenced to tetramethylsilane) of the product is listed as follows: δ 8.06 (s, 1H), 7.67 (m, 4H), 4.01 (s, 3H). From the $^1H$ NMR data, the structure of the product was determined to be as follows:

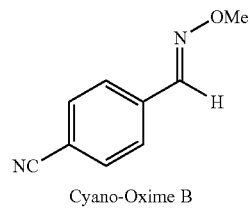 [SMILES: CO/N=C/c1ccc(C#N)cc1]

Cyano-Oxime B

Example 3

Synthesis of Unmodified cis-1,4-Polybutadiene

To a 2-gallon nitrogen-purged reactor equipped with turbine agitator blades were added 1594 g of hexane and 2873 g of 22.0 wt % 1,3-butadiene in hexane. A preformed catalyst was prepared by mixing 7.35 ml of 4.32 M methylaluminoxane in toluene, 1.56 g of 22.0 wt % 1,3-butadiene in hexane, 0.59 ml of 0.537 M neodymium versatate in cyclohexane, 6.67 ml of 1.0 M diisobutylaluminum hydride in hexane, and 1.27 ml of 1.0 M diethylaluminum chloride in hexane. The catalyst was aged for 15 minutes and charged into the reactor. The reactor jacket temperature was then set to 65° C. About 60 minutes after addition of the catalyst, the polymerization mixture was cooled to room temperature and quenched with 30 ml of 12 wt % 2,6-di-tert-butyl-4-methylphenol solution in isopropanol. The resulting polymer cement was coagulated with 12 liters of isopropanol containing 5 g of 2,6-di-tert-butyl-4-methylphenol and then drum-dried. The Mooney viscosity ($ML_{1+4}$) of the resulting polymer was determined to be 25.1 at 100° C. by using an Alpha Technologies Mooney viscometer with a large rotor, a one-minute warm-up time, and a four-minute running time. As determined by gel permeation chromatography (GPC), the polymer had a number average molecular weight ($M_n$) of 107,900, a weight average molecular weight ($M_w$) of 215,600, and a molecular weight distribution ($M_w/M_n$) of 2.00. The infrared spectroscopic analysis of the polymer indicated a cis-1,4-linkage content of 94.5%, a trans-1,4-linkage content of 4.9%, and a 1,2-linkage content of 0.6%.

The properties of the unmodified cis-1,4-polybutadiene are summarized in Table 1.

TABLE 1

Physical Properties of cis-1,4-Polybutadiene

| Example No. | Example 3 | Example 4 | Example 5 | Example 6 |
|---|---|---|---|---|
| Polymer type | unmodified | unmodified | Cyano-Oxime A modified | Cyano-Oxime B modified |
| $ML_{1+4}$ at 100° C. | 25.1 | 44.7 | 34.9 | 28.2 |
| $M_n$ | 107,900 | 137,200 | 91,300 | 107,200 |
| $M_w$ | 215,600 | 266,500 | 236,600 | 199,500 |
| $M_w/M_n$ | 2.00 | 1.94 | 2.59 | 1.86 |
| % cis-1,4-linkage | 94.5 | 96.6 | 95.1 | 95.1 |
| % trans-1,4-linkage | 4.9 | 2.8 | 4.4 | 4.4 |
| % 1,2-linkage | 0.6 | 0.6 | 0.5 | 0.5 |

Example 4

Synthesis of Unmodified cis-1,4-Polybutadiene

To a 2-gallon nitrogen-purged reactor equipped with turbine agitator blades were added 1594 g of hexane and 2873 g of 22.0 wt % 1,3-butadiene in hexane. A preformed catalyst was prepared by mixing 5.14 ml of 4.32 M methylaluminoxane in toluene, 1.09 g of 22.0 wt % 1,3-butadiene in hexane, 0.43 ml of 0.537 M neodymium versatate in cyclohexane, 4.80 ml of 1.0 M diisobutylaluminum hydride in hexane, and 0.89 ml of 1.0 M diethylaluminum chloride in hexane. The catalyst was aged for 15 minutes and charged into the reactor. The reactor jacket temperature was then set to 65° C. About 85 minutes after addition of the catalyst, the polymerization mixture was cooled to room temperature and quenched with 30 ml of 12 wt % 2,6-di-tert-butyl-4-methylphenol solution in isopropanol. The resulting polymer cement was coagulated with 12 liters of isopropanol containing 5 g of 2,6-di-tert-butyl-4-methylphenol and then drum-dried. The properties of the resulting polymer are summarized in Table 1.

Example 5

Synthesis of cis-1,4-Polybutadiene Modified with 2-Cyanobenzaldehyde O-Methyloxime (Cyano-Oxime A)

To a 2-gallon nitrogen-purged reactor equipped with turbine agitator blades were added 1542 g of hexane and 2926 g of 21.7 wt % 1,3-butadiene in hexane. A preformed catalyst was prepared by mixing 7.35 ml of 4.32 M methylaluminoxane in toluene, 1.58 g of 21.7 wt % 1,3-butadiene in hexane, 0.59 ml of 0.537 M neodymium versatate in cyclohexane, 6.67 ml of 1.0 M diisobutylaluminum hydride in hexane, and 1.27 ml of 1.0 M diethylaluminum chloride in hexane. The catalyst was aged for 15 minutes and charged into the reactor. The reactor jacket temperature was then set to 65° C. About 60 minutes after addition of the catalyst, the polymerization mixture was cooled to room temperature.

About 353 g of the resulting unmodified polymer cement (i.e., pseudo-living polymer cement) was transferred from the reactor to a nitrogen-purged bottle, followed by addition of 4.71 ml of 0.42 M 2-cyanobenzaldehyde O-methyloxime (cyano-oxime A) in toluene. The bottle was tumbled for 30 minutes in a water bath maintained at 65° C. The resulting polymer cement was quenched with 3 ml of 12 wt % 2,6-di-tert-butyl-4-methylphenol solution in isopropanol, coagulated with 2 liters of isopropanol containing 0.5 g of 2,6-di-tert-butyl-4-methylphenol, and then drum-dried. The properties of the resulting polymer are summarized in Table 1.

Example 6

Synthesis of cis-1,4-Polybutadiene Modified with 4-Cyanobenzaldehyde O-Methyloxime (Cyano-Oxime B)

About 358 g of the pseudo-living polymer cement as synthesized in Example 5 was transferred from the reactor to a nitrogen-purged bottle, followed by addition of 4.67 ml of 0.43 M 4-cyanobenzaldehyde O-methyloxime (cyano-oxime B) in toluene in toluene. The bottle was tumbled for 30 minutes in a water bath maintained at 65° C. The resulting polymer cement was quenched with 3 ml of 12 wt % 2,6-di-tert-butyl-4-methylphenol solution in isopropanol, coagulated with 2 liters of isopropanol containing 0.5 g of 2,6-di-tert-butyl-4-methylphenol, and then drum-dried. The properties of the resulting polymer are summarized in Table 1.

Examples 7-10

Compounding Evaluation of cis-1,4-Polybutadiene Modified with Cyano-Oxime A and Cyano-Oxime B vs. Unmodified cis-1,4-Polybutadiene The cis-1,4-polybutadiene samples produced in Examples 3-6 were evaluated in a rubber compound filled with carbon black. The compositions of the vulcanizates are presented in Table 2, wherein the numbers are expressed as parts by weight per hundred parts by weight of total rubber (phr).

TABLE 2

Compositions of Rubber Vulcanizates Prepared from cis-1,4-Polybutadiene

| Ingredient | Amount (phr) |
|---|---|
| cis-1,4-Polybutadiene sample | 80 |
| Polyisoprene | 20 |
| HAF Carbon black | 50 |
| Oil | 10 |
| Wax | 2 |
| Antioxidant | 1 |
| Zinc oxide | 2.5 |
| Stearic acid | 2 |
| Accelerators | 1.3 |
| Sulfur | 1.5 |
| Total | 170.3 |

The Mooney viscosity (ML1+4) of the uncured rubber compound was determined at 130° C. by using an Alpha Technologies Mooney viscometer with a large rotor, a one-minute warm-up time, and a four-minute running time. The tensile mechanical properties (modulus, $T_b$, and $E_b$) of the vulcanizates were measured by using the standard procedure described in ASTM-D412. The hysteresis data (tan δ) and the Payne effect data (ΔG') of the vulcanizates were obtained from a dynamic strain-sweep experiment, which was conducted at 50° C. and 15 Hz with strain sweeping from 0.1% to 20%. ΔG' is the difference between G' at 0.1% strain and G' at 20% strain. The physical properties of the vulcanizates are summarized in Table 3. In the FIGURE, the tan δ data are plotted against the compound Mooney viscosities.

Table 3

| Physical Properties of Rubber Vulcanizates Prepared from cis-1,4-Polybutadiene | | | | |
|---|---|---|---|---|
| Example No. | Example 7 | Example 8 | Example 9 | Example 10 |
| Polymer used | Example 3 | Example 4 | Example 5 | Example 6 |
| Polymer type | unmodified | unmodified | cyano-oxime A modified | cyano-oxime B modified |
| Compound $ML_{1+4}$ at 130° C. | 47.4 | 66.8 | 59.2 | 53.5 |
| 300% modulus at 23° C. (MPa) | 7.77 | 8.51 | 8.38 | 8.11 |
| $T_b$ at 23° C. (MPa) | 12.7 | 15.7 | 14.7 | 14.4 |
| $E_b$ at 23° C. (%) | 417 | 457 | 438 | 446 |
| tanδ at 50° C., 3% strain | 0.147 | 0.119 | 0.117 | 0.117 |
| ΔG' (MPa) | 3.04 | 2.51 | 1.95 | 1.86 |

As can be seen in Table 3 and the FIGURE, at the same compound Mooney viscosity, the cis-1,4-polybutadiene samples modified with cyano-oxime A and cyano-oxime B give lower tan δ than the unmodified polymer, indicating that the modification of cis-1,4-polybutadiene with cyano-oxime A and cyano-oxime B reduces hysteresis. At the same compound Mooney viscosity, the cis-1,4-polybutadiene samples modified with cyano-oxime A and cyano-oxime B also give lower ΔG' than the unmodified polymer, indicating that the Payne Effect has been reduced due to the stronger interaction between the modified polymer and carbon black.

Various modifications and alterations that do not depart from the scope and spirit of this invention will become apparent to those skilled in the art. This invention is not to be duly limited to the illustrative embodiments set forth herein.

What is claimed is:

1. A method for preparing a functionalized polymer, the method comprising the steps of:
   (i) polymerizing monomer to form a reactive polymer, and
   (ii) reacting the reactive polymer with a protected oxime compound containing a cyano group.

2. The method of claim 1, where the protected oxime compound containing a cyano group is defined by the formula I:

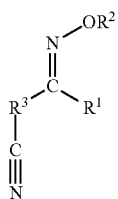

where $R^1$ is a hydrogen atom or monovalent organic group, $R^2$ is a monovalent organic group, and $R^3$ is a bond or a divalent organic group, or where $R^1$ and $R^3$ join to form a trivalent organic group.

3. The method of claim 2, where the protected oxime compound containing a cyano group is defined by the formula II:

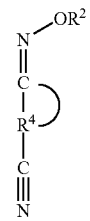

where $R^2$ is a monovalent organic group and $R^4$ is a trivalent organic group.

4. The method of claim 1, where the protected oxime compound containing a cyano group is selected from the group consisting of cyano O-hydrocarbyloximes, cyano O-silyloximes, cyano O-sulfonyloximes, and cyano O-acyloximes.

5. The method of claim 4, where the protected oxime compound containing a cyano group is a cyano O-hydrocarbyloxime selected from the group consisting of cyanoformaldehyde O-methyloxime, 2-cyanoacetaldehyde O-methyloxime, 2-cyanopropionaldehyde O-methyloxime, 3-cyanobutyraldehyde O-methyloxime, 3-cyanopentanaldehyde O-methyloxime, 2-cyanocyclopentanecarboxaldehyde O-methyloxime, 6-cyanohexanaldehyde O-methyloxime, 3-cyanocyclohexanecarboxaldehyde O-methyloxime, 6-cyanoheptanaldehyde O-methyloxime, 4-cyanocycloheptanecarboxaldehyde O-methyloxime, 6-cyanooctanaldehyde O-methyloxime, 4-cyanocyclooctanecarboxaldehyde O-methyloxime, 9-cyanononanaldehyde O-methyloxime, 3-cyanocyclononanecarboxaldehyde O-methyloxime, 2-cyanobenzaldehyde O-methyloxime, 3-cyanobenzaldehyde O-methyloxime, 4-cyanobenzaldehyde O-methyloxime, 4-cyano-trans-cinnamaldehyde O-methyloxime, 4-cyano-2-pyridinecarboxaldehyde O-methyloxime, 4-cyanotetrahydrofuran-3-carboxaldehyde O-methyloxime, 4-cyano-2-furancarboxaldehyde O-methyloxime, 2-cyano-3-furancarboxaldehyde O-methyloxime, 3-cyano-N-methyl-4-pyrazolecarboxaldehyde O-methyloxime, 4-cyano-N-methyl-2-pyrrolecarboxaldehyde O-methyloxime, 4-cyano-N-methyl-2-imidazolecarboxaldehyde O-methyloxime, 5-cyano-N-methyl-indole-3-carboxaldehyde O-methyloxime, 5-cyano-N-methyl-1,2,3-triazole-4-carboxaldehyde O-methyloxime, 5-cyano-N-methyl-1,2,4-triazole-3-carboxaldehyde O-methyloxime, 3-cyanopyrazinecarboxaldehyde O-methyloxime, 4-cyano-2-thiazolecarboxaldehyde O-methyloxime, 4-cyano-2-thiophenecarboxaldehyde O-methyloxime, cyanoformaldehyde O-benzyloxime, 2-cyanoacetaldehyde O-benzyloxime, 2-cyanopropionaldehyde O-benzyloxime, 3-cyanobutyraldehyde O-benzyloxime, 3-cyanopentanaldehyde O-benzyloxime, 2-cyanocyclopentanecarboxaldehyde O-benzyloxime, 6-cyanohexanaldehyde O-benzyloxime, 3-cyanocyclohexanecarboxaldehyde O-benzyloxime, 6-cyanoheptanaldehyde O-benzyloxime, 4-cyanocycloheptanecarboxaldehyde O-benzyloxime, 6-cyanooctanaldehyde O-benzyloxime, 4-cyanocyclooctanecarboxaldehyde O-benzyloxime, 9-cyanononanaldehyde O-benzyloxime, 3-cyanocyclononanecarboxaldehyde O-benzyloxime, 2-cyanobenzaldehyde O-benzyloxime, 3-cyanobenzaldehyde O-benzyloxime, 4-cyanobenzaldehyde O-benzyloxime, 4-cyano-trans-cinnamaldehyde O-benzyloxime, 4-cyano-2-pyridinecarboxaldehyde O-benzyloxime, 4-cyanotetrahydrofuran-3-carboxaldehyde O-benzyloxime, 4-cyano-2-furancarboxaldehyde O-benzyloxime, 2-cyano-3-furancarboxaldehyde O-benzyloxime, 3-cyano-N-methyl-4-pyrazolecarboxaldehyde O-benzyloxime, 4-cyano-N-methyl-2-pyrrolecarboxaldehyde O-benzyloxime, 4-cyano-N-methyl-2-imidazolecarboxaldehyde O-benzyloxime, 5-cyano-N-methyl-indole-3-carboxaldehyde O-benzyloxime, 5-cyano-N-methyl-1,2,3-triazole-4-carboxaldehyde O-benzyloxime, 5-cyano-N-methyl-1,2,4-triazole-3-carboxaldehyde O-benzyloxime, 3-cyanopyrazinecarboxaldehyde O-benzyloxime, 4-cyano-2-thiazolecarboxaldehyde O-benzyloxime, 4-cyano-2-thiophenecarboxaldehyde O-benzyloxime, 1-cyano-2-propanone O-methyloxime, 4-cyano-2-butanone O-methyloxime, 3-cyano-2-pentanone O-methyloxime, 1-cyano-3-pentanone O-methyloxime, 4-cyano-2-hexanone O-methyloxime, 1-cyano-3-hexanone O-methyloxime, 4-cyano-2-heptanone O-methyloxime, 1-cyano-3-heptanone O-methyloxime, 1-cyano-4-heptanone O-methyloxime, 5-cyano-2-octanone O-methyloxime, 5-cyano-3-octanone O-methyloxime, 9-cyano-2-nonanone O-methyloxime, 6-cyano-3-nonanone O-methyloxime, 1-cyano-5-nonanone O-methyloxime, 1-(2-cyanophenyl)ethan-1-one O-methyloxime, 1-(3-cyanophenyl)ethan-1-one O-methyloxime, 1-(4-cyanophenyl)ethan-1-one O-methyloxime, 1-(2-cyanocyclohexyl)ethan-1-one O-methyloxime, 1-(3-cyanocyclohexyl)ethan-1-one O-methyloxime, 1-(4-cyanocyclohexyl)ethan-1-one O-methyloxime, 2-cyanoacetophenone O-methyloxime, 3-cyanobenzophenone O-methyloxime, 4-cyanobenzophenone O-methyloxime, 2-cyanocyclobutanone O-methyloxime, 3-cyanocyclopentanone O-methyloxime, 2-cyanocyclohexanone O-methyloxime, 3-cyanocycloheptanone O-methyloxime, 4-cyanocyclooctanone O-methyloxime, 3-cyanocyclononanone O-methyloxime, 2-cyanocyclodecanone O-methyloxime, 4-cyanocycloundecanone O-methyloxime, 3-cyanocyclododecanone O-methyloxime, 4-cyanocyclotridecanone O-methyloxime, 4-cyano-1,3-dimethyl-2-imidazolidinone O-methyloxime, 1-(3-cyanothiophen-2-yl)ethan-1-one O-methyloxime, 1-(4-cyanothiazol-2-yl)ethan-1-one O-methyloxime, 1-(3-cyanopyridin-2-yl)ethan-1-one O-methyloxime, 1-(4-cyanopyridin-3-yl)ethan-1-one O-methyloxime, 1-(3-cyanopyridin-4-yl)ethan-1-one O-methyloxime, 4-cyano-bis(2-pyridyl)ketone O-methyloxime, 1-(3-cyano-1-methylpyrrolyl)ethan-1-one O-methyloxime, 1-(2-cyano-1-methylpyrrolyl)ethan-1-one O-methyloxime, 1-cyano-2-propanone O-benzyloxime, 4-cyano-2-butanone O-benzyloxime, 3-cyano-2-pentanone O-benzyloxime, 1-cyano-3-pentanone O-benzyloxime, 4-cyano-2-hexanone O-benzyloxime, 1-cyano-3-hexanone O-benzyloxime, 4-cyano-2-heptanone O-benzyloxime, 1-cyano-3-heptanone O-benzyloxime, 1-cyano-4-heptanone O-benzyloxime, 5-cyano-2-octanone O-benzyloxime, 5-cyano-3-octanone O-benzyloxime, 9-cyano-2-nonanone O-benzyloxime, 6-cyano-3-nonanone O-benzyloxime, 1-cyano-5-nonanone O-benzyloxime, 1-(2-cyanophenyl)ethan-1-one O-benzyloxime, 1-(3-cyanophenyl) ethan-1-one O-benzyloxime, 1-(4-cyanophenyl)ethan-1-one O-benzyloxime, 1-(2-cyanocyclohexyl)ethan-1-one O-benzyloxime, 1-(3-cyanocyclohexyl)ethan-1-one O-benzyloxime, 1-(4-cyanocyclohexyl)ethan-1-one O-benzyloxime, 2-cyanoacetophenone O-benzyloxime, 3-cyanobenzophenone O-benzyloxime, 4-cyanobenzophenone O-benzyloxime, 2-cyanocyclobutanone O-benzyloxime, 3-cyanocyclopentanone O-benzyloxime, 2-cyanocyclohexanone O-benzyloxime, 3-cyanocycloheptanone O-benzyloxime, 4-cyanocyclooctanone O-benzyloxime, 3-cyanocyclononanone O-benzyloxime, 2-cyanocyclodecanone O-benzyloxime, 4-cyanocycloundecanone O-benzyloxime, 3-cyanocyclododecanone O-benzyloxime, 4-cyanocyclotridecanone O-benzyloxime, 4-cyano-1,3-dimethyl-2-imidazolidinone O-benzyloxime, 1-(3-cyanothiophen-2-yl)ethan-1-one O-benzyloxime, 1-(4-cyanothiazol-2-yl)ethan-1-one O-benzyloxime, 1-(3-cyanopyridin-2-yl)ethan-1-one O-benzyloxime, 1-(4-cyanopyridin-3-yl)ethan-1-one O-benzyloxime, 1-(3-cyanopyridin-4-yl)ethan-1-one O-benzyloxime, 4-cyano-bis(2-pyridyl)ketone O-benzyloxime, 1-(3-cyano-1-methylpyrrolyl)ethan-1-one O-benzyloxime, and 1-(2-cyano-1-methylpyrrolyl)ethan-1-one O-benzyloxime.

6. The method of claim 4, where the protected oxime compound containing a cyano group is a cyano O-silyloxime selected from the group consisting of cyanoformaldehyde O-trimethylsilyloxime, 2-cyanoacetaldehyde O-trimethylsilyloxime, 2-cyanopropionaldehyde O-trimethylsilyloxime, 3-cyanobutyraldehyde O-trimethylsilyloxime, 3-cyanopentanaldehyde O-trimethylsilyloxime, 2-cyanocyclopentanecarboxaldehyde O-trimethylsilyloxime, 6-cyanohexanaldehyde O-trimethylsilyloxime, 3-cyanocyclohexanecarboxaldehyde O-trimethylsilyloxime, 6-cyanoheptanaldehyde O-trimethylsilyloxime, 4-cyanocycloheptanecarboxaldehyde O-trimethylsilyloxime, 6-cyanooctanaldehyde O-trimethylsilyloxime, 4-cyanocyclooctanecarboxaldehyde O-trimethylsilyloxime, 9-cyanononanaldehyde O-trimethylsilyloxime, 3-cyanocyclononanecarboxaldehyde O-trimethylsilyloxime, 2-cyanobenzaldehyde O-trimethylsilyloxime, 3-cyanobenzaldehyde O-trimethylsilyloxime, 4-cyanobenzaldehyde O-trimethylsilyloxime, 4-cyano-trans-cinnamaldehyde O-trimethylsilyloxime, 4-cyano-2-pyridinecarboxaldehyde O-trimethylsilyloxime, 4-cyanotetrahydrofuran-3-carboxaldehyde O-trimethylsilyloxime, 4-cyano-2-furancarboxaldehyde O-trimethylsilyloxime, 2-cyano-3-furancarboxaldehyde O-trimethylsilyloxime, 3-cyano-N-methyl-4-pyrazolecarboxaldehyde O-trimethylsilyloxime, 4-cyano-N-methyl-2-pyrrolecarboxaldehyde O-trimethylsilyloxime, 4-cyano-N-methyl-2-imidazolecarboxaldehyde O-trimethylsilyloxime, 5-cyano-N-methyl-indole-3-carboxaldehyde O-trimethylsilyloxime, 5-cyano-N-methyl-1,2,3-triazole-4-carboxaldehyde O-trimethylsilyloxime, 5-cyano-N-methyl-1,2,4-triazole-3-carboxaldehyde O-trimethylsilyloxime, 3-cyanopyrazinecarboxaldehyde O-trimethylsilyloxime, 4-cyano-2-thiazolecarboxaldehyde O-trimethylsilyloxime, 4-cyano-2-thiophenecarboxaldehyde O-trimethylsilyloxime, cyanoformaldehyde O-triphenylsilyloxime, 2-cyanoacetaldehyde O-triphenylsilyloxime, 2-cyanopropionaldehyde O-triphenylsilyloxime, 3-cyanobutyraldehyde O-triphenylsilyloxime, 3-cyanopentanaldehyde O-triphenylsilyloxime, 2-cyanocyclopentanecarboxaldehyde O-triphenylsilyloxime, 6-cyanohexanaldehyde O-triphenylsilyloxime, 3-cyanocyclohexanecarboxaldehyde O-triphenylsilyloxime, 6-cyanoheptanaldehyde O-triphenylsilyloxime, 4-cyanocycloheptanecarboxaldehyde O-triphenylsilyloxime, 6-cyanooctanaldehyde O-triphenylsilyloxime, 4-cyanocyclooctanecarboxaldehyde O-triphenylsilyloxime, 9-cyanononanaldehyde O-triphenylsilyloxime, 3-cyanocyclononanecarboxaldehyde O-triphenylsilyloxime, 2-cyanobenzaldehyde O-triphenylsilyloxime, 3-cyanobenzaldehyde O-triphenylsilyloxime, 4-cyanobenzaldehyde O-triphenylsilyloxime, 4-cyano-trans-cinnamaldehyde O-triphenylsilyloxime, 4-cyano-2-pyridinecarboxaldehyde O-triphenylsilyloxime, 4-cyanotetrahydrofuran-3-carboxaldehyde O-triphenylsilyloxime, 4-cyano-2-furancarboxaldehyde O-triphenylsilyloxime, 2-cyano-3-furancarboxaldehyde O-triphenylsilyloxime, 3-cyano-N-methyl-4- pyrazolecarboxaldehyde O-triphenylsilyloxime, 4-cyano-N-methyl-2-pyrrolecarboxaldehyde O-triphenylsilyloxime, 4-cyano-N-methyl-2-imidazolecarboxaldehyde O-triphenylsilyloxime, 5-cyano-N-methyl-indole-3-carboxaldehyde O-triphenylsilyloxime, 5-cyano-N-methyl-1,2,3-triazole-4-carboxaldehyde O-triphenylsilyloxime, 5-cyano-N-methyl-1,2,4-triazole-3-carboxaldehyde O-triphenylsilyloxime, 3-cyanopyrazinecarboxaldehyde O-triphenylsilyloxime, 4-cyano-2-thiazolecarboxaldehyde O-triphenylsilyloxime, 4-cyano-2-thiophenecarboxaldehyde O-triphenylsilyloxime, 1-cyano-2-propanone O-trimethylsilyloxime, 4-cyano-2-butanone O-trimethylsilyloxime, 3-cyano-2-pentanone O-trimethylsilyloxime, 1-cyano-3-pentanone O-trimethylsilyloxime, 4-cyano-2-hexanone O-trimethylsilyloxime, 1-cyano-3-hexanone O-trimethylsilyloxime, 4-cyano-2-heptanone O-trimethylsilyloxime, 1-cyano-3-heptanone O-trimethylsilyloxime, 1-cyano-4-heptanone O-trimethylsilyloxime, 5-cyano-2-octanone O-trimethylsilyloxime, 5-cyano-3-octanone O-trimethylsilyloxime, 9-cyano-2-nonanone O-trimethylsilyloxime, 6-cyano-3-nonanone O-trimethylsilyloxime, 1-cyano-5-nonanone O-trimethylsilyloxime, 1-(2-cyanophenyl)ethan-1-one O-trimethylsilyloxime, 1-(3-cyanophenyl) ethan-1-one O-trimethylsilyloxime, 1-(4-cyanophenyl)ethan-1-one O-trimethylsilyloxime, 1-(2-cyanocyclohexyl)ethan-1-one O-trimethylsilyloxime, 1-(3-cyanocyclohexyl)ethan-1-one O-trimethylsilyloxime, 1-(4-cyanocyclohexyl)ethan-1-one O-trimethylsilyloxime, 2-cyanoacetophenone O-trimethylsilyloxime, 3-cyanobenzophenone O-trimethylsilyloxime, 4-cyanobenzophenone O-trimethylsilyloxime, 2-cyanocyclobutanone O-trimethylsilyloxime, 3-cyanocyclopentanone O-trimethylsilyloxime, 2-cyanocyclohexanone O-trimethylsilyloxime, 3-cyanocycloheptanone O-trimethylsilyloxime, 4-cyanocyclooctanone O-trimethylsilyloxime, 3-cyanocyclononanone O-trimethylsilyloxime, 2-cyanocyclodecanone O-trimethylsilyloxime, 4-cyanocycloundecanone O-trimethylsilyloxime, 3-cyanocyclododecanone O-trimethylsilyloxime, 4-cyanocyclotridecanone O-trimethylsilyloxime, 4-cyano-1,3-dimethyl-2-imidazolidinone O-trimethylsilyloxime, 1-(3-cyanothiophen-2-yl)ethan-1-one O-trimethylsilyloxime, 1-(4-cyanothiazol-2-yl)ethan-1-one O-trimethylsilyloxime, 1-(3-cyanopyridin-2-yl)ethan-1-one O-trimethylsilyloxime, 1-(4-cyanopyridin-3-yl)ethan-1-one O-trimethylsilyloxime, 1-(3-cyanopyridin-4-yl)ethan-1-one O-trimethylsilyloxime, 4-cyano-bis(2-pyridyl)ketone O-trimethylsilyloxime, 1-(3-cyano-1-methylpyrrolyl)ethan-1-one O-trimethylsilyloxime, 1-(2-cyano-1-methylpyrrolyl)ethan-1-one O-trimethylsilyloxime, 1-cyano-2-propanone O-triphenylsilyloxime, 4-cyano-2-butanone O-triphenylsilyloxime, 3-cyano-2-pentanone O-triphenylsilyloxime, 1-cyano-3-pentanone O-triphenylsilyloxime, 4-cyano-2-hexanone O-triphenylsilyloxime, 1-cyano-3-hexanone O-triphenylsilyloxime, 4-cyano-2-heptanone O-triphenylsilyloxime, 1-cyano-3-heptanone O-triphenylsilyloxime, 1-cyano-4-heptanone O-triphenylsilyloxime, 5-cyano-2-octanone O-triphenylsilyloxime, 5-cyano-3-octanone O-triphenylsilyloxime, 9-cyano-2-nonanone O-triphenylsilyloxime, 6-cyano-3-nonanone O-triphenylsilyloxime, 1-cyano-5-nonanone O-triphenylsilyloxime, 1-(2-cyanophenyl) ethan-1-one O-triphenylsilyloxime, 1-(3-cyanophenyl) ethan-1-one O-triphenylsilyloxime, 1-(4-cyanophenyl) ethan-1-one O-triphenylsilyloxime, 1-(2-cyanocyclohexyl) ethan-1-one O-triphenylsilyloxime, 1-(3-cyanocyclohexyl) ethan-1-one O-triphenylsilyloxime, 1-(4-cyanocyclohexyl) ethan-1-one O-triphenylsilyloxime, 2-cyanoacetophenone O-triphenylsilyloxime, 3-cyanobenzophenone O-triphenylsilyloxime, 4-cyanobenzophenone O-triphenylsilyloxime, 2-cyanocyclobutanone O-triphenylsilyloxime, 3-cyanocyclopentanone O-triphenylsilyloxime, 2-cyanocyclohexanone O-triphenylsilyloxime, 3-cyanocycloheptanone O-triphenylsilyloxime, 4-cyanocyclooctanone O-triphenylsilyloxime, 3-cyanocyclononanone O-triphenylsilyloxime, 2-cyanocyclodecanone O-triphenylsilyloxime, 4-cyanocycloundecanone O-triphenylsilyloxime, 3-cyanocyclododecanone O-triphenylsilyloxime, 4-cyanocyclotridecanone O-triphenylsilyloxime, 4-cyano-1,3-dimethyl-2-imidazolidinone O-triphenylsilyloxime, 1-(3-cyanothiophen-2-yl)ethan-1-one O-triphenylsilyloxime, 1-(4-cyanothiazol-2-yl)ethan-1-one O-triphenylsilyloxime, 1-(3-cyanopyridin-2-yl)ethan-1-one O-triphenylsilyloxime, 1-(4-cyanopyridin-3-yl)ethan-1-one O-triphenylsilyloxime, 1-(3-cyanopyridin-4-yl)ethan-1-one O-triphenylsilyloxime, 4-cyano-bis(2-pyridyl) ketone O-triphenylsilyloxime, 1-(3-cyano-1-methylpyrrolyl)ethan-1-one O-triphenylsilyloxime, and 1-(2-cyano-1-methylpyrrolyl)ethan-1-one O-triphenylsilyloxime.

7. The method of claim 4, where the protected oxime compound containing a cyano group is a cyano O-sulfonyloxime selected from the group consisting of cyanoformaldehyde O-benzenesulfonyloxime, 2-cyanoacetaldehyde O-benzenesulfonyloxime, 2-cyanopropionaldehyde O-benzenesulfonyloxime, 3-cyanobutyraldehyde O-benzenesulfonyloxime, 3-cyanopentanaldehyde O-benzenesulfonyloxime, 2-cyanocyclopentanecarboxaldehyde O-benzenesulfonyloxime, 6-cyanohexanaldehyde O-benzenesulfonyloxime, 3-cyanocyclohexanecarboxaldehyde O-benzenesulfonyloxime, 6-cyanoheptanaldehyde O-benzenesulfonyloxime, 4-cyanocycloheptanecarboxaldehyde O-benzenesulfonyloxime, 6-cyanooctanaldehyde O-benzenesulfonyloxime, 4-cyanocyclooctanecarboxaldehyde O-benzenesulfonyloxime, 9-cyanononanaldehyde O-benzenesulfonyloxime, 3-cyanocyclononanecarboxaldehyde O-benzenesulfonyloxime, 2-cyanobenzaldehyde O-benzenesulfonyloxime, 3-cyanobenzaldehyde O-benzenesulfonyloxime, 4-cyanobenzaldehyde O-benzenesulfonyloxime, 4-cyano-trans-cinnamaldehyde O-benzenesulfonyloxime, 4-cyano-2-pyridinecarboxaldehyde O-benzenesulfonyloxime, 4-cyanotetrahydrofuran-3-carboxaldehyde O-benzenesulfonyloxime, 4-cyano-2-furancarboxaldehyde O-benzenesulfonyloxime, 2-cyano-3-furancarboxaldehyde O-benzenesulfonyloxime, 3-cyano-N-methyl-4-pyrazolecarboxaldehyde O-benzenesulfonyloxime, 4-cyano-N-methyl-2-pyrrolecarboxaldehyde O-benzenesulfonyloxime, 4-cyano-N-methyl-2-imidazolecarboxaldehyde O-benzenesulfonyloxime, 5-cyano-N-methyl-indole-3-carboxaldehyde O-benzenesulfonyloxime, 5-cyano-N-methyl-1,2,3-triazole-4-carboxaldehyde O-benzenesulfonyloxime, 5-cyano-N-methyl-1,2,4-triazole-3-carboxaldehyde O-benzenesulfonyloxime, 3-cyanopyrazinecarboxaldehyde O-benzenesulfonyloxime, 4-cyano-2-thiazolecarboxaldehyde O-benzenesulfonyloxime, 4-cyano-2-thiophenecarboxaldehyde O-benzenesulfonyloxime, 1-cyano-2-propanone O-benzenesulfonyloxime, 4-cyano-2-butanone O-benzenesulfonyloxime, 3-cyano-2-pentanone O-benzenesulfonyloxime, 1-cyano-3-pentanone O-benzenesulfonyloxime, 4-cyano-2-hexanone O-benzenesulfonyloxime, 1-cyano-3-hexanone O-benzenesulfonyloxime, 4-cyano-2-heptanone O-benzenesulfonyloxime, 1-cyano-3-heptanone O-benzenesulfonyloxime, 1-cyano-4-heptanone O-benzenesulfonyloxime, 5-cyano-2-octanone O-benzenesulfonyloxime, 5-cyano-3-octanone O-benzenesulfonyloxime, 9-cyano-2-nonanone O-benzenesulfonyloxime, 6-cyano-3-nonanone O-benzenesulfonyloxime, 1-cyano-5-nonanone O-benzenesulfonyloxime, 1-(2-cyanophenyl)ethan-1-one O-benzenesulfonyloxime, 1-(3-cyanophenyl)ethan-1-one O-benzenesulfonyloxime, 1-(4-cyanophenyl)ethan-1-one O-benzenesulfonyloxime, 1-(2-cyanocyclohexyl)ethan-1-one O-benzenesulfonyloxime, 1-(3-cyanocyclohexyl)ethan-1-one O-benzenesulfonyloxime, 1-(4-cyanocyclohexyl)ethan-1-one O-benzenesulfonyloxime, 2-cyanoacetophenone O-benzenesulfonyloxime, 3-cyanobenzophenone O-benzenesulfonyloxime, 4-cyanobenzophenone O-benzenesulfonyloxime, 2-cyanocyclobutanone O-benzenesulfonyloxime, 3-cyanocyclopentanone O-benzenesulfonyloxime, 2-cyanocyclohexanone O-benzenesulfonyloxime, 3-cyanocycloheptanone O-benzenesulfonyloxime, 4-cyanocyclooctanone O-benzenesulfonyloxime, 3-cyanocyclononanone O-benzenesulfonyloxime, 2-cyanocyclodecanone O-benzenesulfonyloxime, 4-cyanocycloundecanone O-benzenesulfonyloxime, 3-cyanocyclododecanone O-benzenesulfonyloxime, 4-cyanocyclotridecanone O-benzenesulfonyloxime, 4-cyano-1,3-dimethyl-2-imidazolidinone O-benzenesulfonyloxime, 1-(3-cyanothiophen-2-yl)ethan-1-one O-benzenesulfonyloxime, 1-(4-cyanothiazol-2-yl)ethan-1-one O-benzenesulfonyloxime, 1-(3-cyanopyridin-2-yl)ethan-1-one O-benzenesulfonyloxime, 1-(4-cyanopyridin-3-yl)ethan-1-one O-benzenesulfonyloxime, 1-(3-cyanopyridin-4-yl)ethan-1-one O-benzenesulfonyloxime, 4-cyano-bis(2-pyridyl)ketone O-benzenesulfonyloxime, 1-(3-cyano-1-methylpyrrolyl)ethan-1-one O-benzenesulfonyloxime, and 1-(2-cyano-1-methylpyrrolyl)ethan-1-one O-benzenesulfonyloxime.

8. The method of claim 4, where the protected oxime compound containing a cyano group is a cyano O-acyloxime selected from the group consisting of cyanoformaldehyde O-acetyloxime, 2-cyanoacetaldehyde O-acetyloxime, 2-cyanopropionaldehyde O-acetyloxime, 3-cyanobutyraldehyde O-acetyloxime, 3-cyanopentanaldehyde O-acetyloxime, 2-cyanocyclopentanecarboxaldehyde O-acetyloxime, 6-cyanohexanaldehyde O-acetyloxime, 3-cyanocyclohexanecarboxaldehyde O-acetyloxime, 6-cyanoheptanaldehyde O-acetyloxime, 4-cyanocycloheptanecarboxaldehyde O-acetyloxime, 6-cyanooctanaldehyde O-acetyloxime, 4-cyanocyclooctanecarboxaldehyde O-acetyloxime, 9-cyanononanaldehyde O-acetyloxime, 3-cyanocyclononanecarboxaldehyde O-acetyloxime, 2-cyanobenzaldehyde O-acetyloxime, 3-cyanobenzaldehyde O-acetyloxime, 4-cyanobenzaldehyde O-acetyloxime, 4-cyano-trans-cinnamaldehyde O-acetyloxime, 4-cyano-2-pyridinecarboxaldehyde O-acetyloxime, 4-cyanotetrahydrofuran-3-carboxaldehyde O-acetyloxime, 4-cyano-2-furancarboxaldehyde O-acetyloxime, 2-cyano-3-furancarboxaldehyde O-acetyloxime, 3-cyano-N-methyl-4-pyrazolecarboxaldehyde O-acetyloxime, 4-cyano-N-methyl-2-pyrrolecarboxaldehyde O-acetyloxime, 4-cyano-N-methyl-2-imidazolecarboxaldehyde O-acetyloxime, 5-cyano-N-methyl-indole-3-carboxaldehyde O-acetyloxime, 5-cyano-N-methyl-1,2,3-triazole-4-carboxaldehyde O-acetyloxime, 5-cyano-N-methyl-1,2,4-triazole-3-carboxaldehyde O-acetyloxime, 3-cyanopyrazinecarboxaldehyde O-acetyloxime, 4-cyano-2-thiazolecarboxaldehyde O-acetyloxime, 4-cyano-2-thiophenecarboxaldehyde O-acetyloxime, 1-cyano-2-propanone O-acetyloxime, 4-cyano-2-butanone O-acetyloxime, 3-cyano-2-pentanone O-acetyloxime, 1-cyano-3-pentanone O-acetyloxime, 4-cyano-2-hexanone O-acetyloxime, 1-cyano-3-hexanone O-acetyloxime, 4-cyano-2-heptanone O-acetyloxime, 1-cyano-3-heptanone O-acetyloxime, 1-cyano-4-heptanone O-acetyloxime, 5-cyano-2-octanone O-acetyloxime, 5-cyano-3-octanone O-acetyloxime, 9-cyano-2-nonanone O-acetyloxime, 6-cyano-3-nonanone O-acetyloxime, 1-cyano-5-nonanone O-acetyloxime, 1-(2-cyanophenyl)ethan-1-one O-acetyloxime, 1-(3-cyanophenyl)ethan-1-one O-acetyloxime, 1-(4-cyanophenyl)ethan-1-one O-acetyloxime, 1-(2-cyanocyclohexyl)ethan-1-one O-acetyloxime, 1-(3-cyanocyclohexyl)ethan-1-one O-acetyloxime, 1-(4-cyanocyclohexyl)ethan-1-one O-acetyloxime, 2-cyanoacetophenone O-acetyloxime, 3-cyanobenzophenone O-acetyloxime, 4-cyanobenzophenone O-acetyloxime, 2-cyanocyclobutanone O-acetyloxime, 3-cyanocyclopentanone O-acetyloxime, 2-cyanocyclohexanone O-acetyloxime, 3-cyanocycloheptanone O-acetyloxime, 4-cyanocyclooctanone O-acetyloxime, 3-cyanocyclononanone O-acetyloxime, 2-cyanocyclodecanone O-acetyloxime, 4-cyanocycloundecanone O-acetyloxime, 3-cyanocyclododecanone O-acetyloxime, 4-cyanocyclotridecanone O-acetyloxime, 4-cyano-1,3-dimethyl-2-imidazolidinone O-acetyloxime, 1-(3-cyanothiophen-2-yl)ethan-1-one O-acetyloxime, 1-(4-cyanothiazol-2-yl)ethan-1-one O-acetyloxime, 1-(3-cyanopyridin-2-yl)ethan-1-one O-acetyloxime, 1-(4-cyanopyridin-3-yl)ethan-1-one O-acetyloxime, 1-(3-cyanopyridin-4-yl)ethan-1-one O-acetyloxime, 4-cyano-bis(2-pyridyl) ketone O-acetyloxime, 1-(3-cyano-1-methylpyrrolyl)ethan-1-one O-acetyloxime, and 1-(2-cyano-1-methylpyrrolyl)ethan-1-one O-acetyloxime.

9. The method of claim 1, where the monomer includes conjugated diene monomer.

10. The method of claim 9, where said step of polymerizing employs a coordination catalyst.

11. The method of claim 10, where the coordination catalyst is a lanthanide-based catalyst.

12. The method of claim 11, where the lanthanide-based catalyst includes (a) a lanthanide-containing compound, (b) an alkylating agent, and (c) a halogen source.

13. The method of claim 12, where the alkylating agent includes an aluminoxane and an organoaluminum compound represented by the formula $AlR_nX_{3-n}$, where each R, which may be the same or different, is a monovalent organic group that is attached to the aluminum atom via a carbon atom, where each X, which may be the same or different, is a hydrogen atom, a halogen atom, a carboxylate group, an alkoxide group, or an aryloxide group, and where n is an integer of 1 to 3.

14. The method of claim 11, where said step of polymerizing monomer takes place within a polymerization mixture including less than 20% by weight of organic solvent.

15. The method of claim 9, where said step of polymerizing employs an anionic initiator.

16. The method of claim 15, where the anionic initiator is an organolithium compound.

17. A method for preparing a functionalized polymer, the method comprising the steps of:
(i) polymerizing conjugated diene monomer, and optionally monomer copolymerizable therewith, to form a polymer having a reactive chain end; and
(ii) reacting the reactive chain end of the polymer with a protected oxime compound containing a cyano group.

18. The method of claim 17, where said step of polymerizing employs a coordination catalyst or an anionic initiator.

19. The method of claim 18, further comprising the step of protonating the polymer after said step of reacting.

20. A functionalized polymer prepared by the steps of:
(i) polymerizing conjugated diene monomer, and optionally monomer copolymerizable therewith, to form a polymer having a reactive chain end; and
(ii) reacting the reactive chain end of the polymer with a protected oxime compound containing a cyano group.

21. A tire component prepared by employing the functionalized polymer of claim 20.

22. A vulcanizable composition comprising:
   the functionalized polymer of claim 20, a filler, and a curative.

* * * * *